(12) United States Patent
Chu et al.

(10) Patent No.: US 8,709,021 B2
(45) Date of Patent: Apr. 29, 2014

(54) SUTURING INSTRUMENT

(75) Inventors: Michael S. H. Chu, Brookline, MA (US); Robert W. Bialobrzeski, Hampton, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1414 days.

(21) Appl. No.: 11/935,175

(22) Filed: Nov. 5, 2007

(65) Prior Publication Data

US 2008/0109015 A1 May 8, 2008

Related U.S. Application Data

(60) Provisional application No. 60/857,615, filed on Nov. 7, 2006.

(51) Int. Cl.
*A61B 17/04* (2006.01)
*A61B 17/12* (2006.01)

(52) U.S. Cl.
USPC .......................................................... 606/144

(58) Field of Classification Search
USPC ........................................ 606/139, 144–150
See application file for complete search history.

(56) References Cited

U.S. PATENT DOCUMENTS

| | | |
|---|---|---|
| 342,773 A | 6/1886 | Bailey |
| 919,138 A | 4/1909 | Drake et al. |
| 1,037,864 A | 9/1912 | Carlson et al. |
| 1,449,087 A | 3/1923 | Bugbee |
| 1,815,725 A | 7/1931 | Pilling et al. |
| 1,822,330 A | 9/1931 | Ainslie |
| 2,577,240 A | 12/1951 | Findley |
| 2,579,192 A | 12/1951 | Kohl |
| 3,013,559 A | 12/1961 | Thomas |
| 3,160,157 A | 12/1964 | Chisman |
| 3,470,875 A | 10/1969 | Johnson |

(Continued)

FOREIGN PATENT DOCUMENTS

| | | |
|---|---|---|
| EP | 0 140 557 A2 | 5/1985 |
| EP | 0 589 409 A1 | 3/1994 |

(Continued)

OTHER PUBLICATIONS

Notification Concerning Transmittal of International Preliminary Report on Patentability (Ch I of the Patent Cooperation Treaty), issued in corresponding international application No. PCT/US2007/083617, mailed May 22, 2009.

(Continued)

*Primary Examiner* — Melanie Tyson

(57) ABSTRACT

A suturing instrument includes a suturing head that is coupled to the shaft of an elongate body member of the instrument by a connector member which may be biased in either a linear orientation along the longitudinal axis of the shaft or any one of a variety of non-linear orientations with respect to the shaft's longitudinal axis. The connector member can comprise a resilient material such that an external force may be applied to the suturing head and move the suturing head from a biased orientation (e.g., linear) to an unbiased orientation (e.g., non-linear). Once the external force is removed, the resiliency of the connector member allows the suturing head to return from the unbiased orientation to the biased orientation. Therefore, a user may adjust the shape of the instrument by applying or removing an external force on the suturing head.

7 Claims, 23 Drawing Sheets

(56) References Cited

U.S. PATENT DOCUMENTS

| | | |
|---|---|---|
| 3,557,780 A | 1/1971 | Sato |
| 3,638,653 A | 2/1972 | Berry |
| 3,840,017 A | 10/1974 | Violante |
| 3,918,455 A | 11/1975 | Coplan |
| 3,946,740 A | 3/1976 | Bassett |
| 3,986,468 A | 10/1976 | Szostak et al. |
| 4,161,951 A | 7/1979 | Scanlan, Jr. |
| 4,164,225 A | 8/1979 | Johnson et al. |
| 4,224,947 A | 9/1980 | Fukuda |
| 4,235,177 A | 11/1980 | Arbuckle |
| 4,235,238 A | 11/1980 | Ogiu et al. |
| 4,236,470 A | 12/1980 | Stenson |
| 4,312,337 A | 1/1982 | Donohue |
| 4,345,601 A | 8/1982 | Fukuda |
| 4,493,323 A | 1/1985 | Albright et al. |
| 4,548,202 A | 10/1985 | Duncan |
| 4,557,265 A | 12/1985 | Andersson |
| 4,579,072 A | 4/1986 | Koike et al. |
| 4,596,249 A | 6/1986 | Freda et al. |
| 4,602,635 A | 7/1986 | Mulhollan et al. |
| 4,621,640 A | 11/1986 | Mulhollan et al. |
| 4,635,638 A | 1/1987 | Weintraub et al. |
| 4,762,260 A | 8/1988 | Richards et al. |
| 4,781,190 A | 11/1988 | Lee |
| 4,890,615 A | 1/1990 | Caspari et al. |
| 4,898,155 A | 2/1990 | Ovil et al. |
| 4,899,746 A | 2/1990 | Brunk |
| 4,923,461 A | 5/1990 | Caspari et al. |
| 4,926,860 A | 5/1990 | Stice et al. |
| 4,935,027 A | 6/1990 | Yoon |
| 4,957,498 A | 9/1990 | Caspari et al. |
| 5,037,433 A | 8/1991 | Wilk et al. |
| 5,042,707 A | 8/1991 | Taheri |
| 5,047,039 A | 9/1991 | Avant et al. |
| 5,067,957 A | 11/1991 | Jervis |
| 5,100,415 A | 3/1992 | Hayhurst |
| 5,100,418 A | 3/1992 | Yoon et al. |
| 5,100,421 A | 3/1992 | Christoudias |
| 5,100,498 A | 3/1992 | Takeuchi et al. |
| 5,188,636 A | 2/1993 | Fedotov |
| 5,254,130 A * | 10/1993 | Poncet et al. ............. 606/206 |
| 5,258,011 A | 11/1993 | Drews |
| 5,281,237 A | 1/1994 | Gimpelson |
| 5,306,281 A | 4/1994 | Beurrier |
| 5,308,353 A | 5/1994 | Beurrier |
| 5,324,298 A | 6/1994 | Phillips et al. |
| 5,336,231 A | 8/1994 | Adair |
| 5,364,408 A | 11/1994 | Gordon |
| 5,386,818 A | 2/1995 | Schneebaum et al. |
| 5,387,221 A | 2/1995 | Bisgaard |
| 5,389,103 A | 2/1995 | Melzer et al. |
| 5,391,174 A | 2/1995 | Weston |
| 5,417,699 A | 5/1995 | Klein et al. |
| 5,417,700 A | 5/1995 | Egan |
| 5,454,823 A | 10/1995 | Richardson et al. |
| 5,458,609 A | 10/1995 | Gordon et al. |
| 5,496,334 A | 3/1996 | Klundt et al. |
| 5,522,820 A | 6/1996 | Caspari et al. |
| 5,527,321 A | 6/1996 | Hinchliffe |
| 5,540,704 A * | 7/1996 | Gordon et al. ............. 606/144 |
| 5,540,705 A | 7/1996 | Meade et al. |
| 5,549,617 A | 8/1996 | Green et al. |
| 5,549,637 A | 8/1996 | Crainich |
| 5,562,686 A | 10/1996 | Sauer et al. |
| 5,573,542 A | 11/1996 | Stevens |
| 5,575,800 A | 11/1996 | Gordon |
| 5,578,044 A | 11/1996 | Gordon et al. |
| 5,591,179 A | 1/1997 | Edelstein |
| 5,593,421 A | 1/1997 | Bauer |
| 5,643,294 A * | 7/1997 | Tovey et al. ............. 606/148 |
| 5,662,664 A | 9/1997 | Gordon et al. |
| 5,662,666 A | 9/1997 | Onuki et al. |
| 5,665,096 A | 9/1997 | Yoon |
| 5,690,653 A | 11/1997 | Richardson et al. |
| 5,700,272 A | 12/1997 | Gordon et al. |
| 5,700,273 A | 12/1997 | Buelna et al. |
| 5,713,910 A | 2/1998 | Gordon et al. |
| 5,741,277 A | 4/1998 | Gordon et al. |
| 5,741,279 A | 4/1998 | Gordon et al. |
| 5,746,753 A | 5/1998 | Sullivan |
| 5,755,727 A | 5/1998 | Kontos |
| 5,759,188 A | 6/1998 | Yoon |
| 5,779,718 A | 7/1998 | Green et al. |
| 5,782,845 A | 7/1998 | Shewchuk |
| 5,827,298 A | 10/1998 | Hart et al. |
| 5,843,001 A | 12/1998 | Goldenberg |
| 5,855,585 A | 1/1999 | Kontos |
| 5,860,992 A | 1/1999 | Daniel et al. |
| 5,899,909 A | 5/1999 | Claren et al. |
| 5,904,692 A | 5/1999 | Steckel et al. |
| 5,908,428 A | 6/1999 | Scirica et al. |
| 5,910,148 A | 6/1999 | Reimels et al. |
| 5,911,727 A | 6/1999 | Taylor |
| 5,919,199 A | 7/1999 | Mers Kelly et al. |
| 5,951,575 A | 9/1999 | Bolduc et al. |
| 5,954,732 A | 9/1999 | Hart et al. |
| 6,048,351 A | 4/2000 | Gordon et al. |
| 6,051,006 A | 4/2000 | Shluzas et al. |
| 6,117,067 A | 9/2000 | Gil-Vernet |
| 6,224,525 B1 | 5/2001 | Stein |
| 6,443,962 B1 | 9/2002 | Gaber |
| 6,454,778 B2 | 9/2002 | Kortenbach |
| 6,743,239 B1 | 6/2004 | Kuehn et al. |
| 6,830,578 B2 | 12/2004 | O'Heeron et al. |
| 7,041,111 B2 | 5/2006 | Chu |
| 2003/0045900 A1 | 3/2003 | Hahnen et al. |
| 2003/0233104 A1 | 12/2003 | Gellman et al. |
| 2005/0251167 A1 | 11/2005 | Voegele et al. |
| 2006/0041263 A1 | 2/2006 | Chu et al. |

FOREIGN PATENT DOCUMENTS

| | | |
|---|---|---|
| EP | 0 674 875 A1 | 10/1995 |
| GB | 2 268 690 A | 1/1994 |
| WO | WO 90/03766 A1 | 4/1990 |
| WO | WO 92/12674 A1 | 8/1992 |
| WO | WO 93/01750 A1 | 2/1993 |
| WO | WO 94/05213 A1 | 3/1994 |
| WO | WO 94/13211 A1 | 6/1994 |
| WO | WO 96/09796 A2 | 4/1996 |
| WO | WO 96/27331 A1 | 9/1996 |
| WO | WO 98/48713 | 11/1998 |
| WO | WO 99/47050 A2 | 9/1999 |
| WO | WO 01/28432 A1 | 4/2001 |
| WO | WO 03/105701 A2 | 12/2003 |

OTHER PUBLICATIONS

Notification of Transmittal of the International Search Report and the Written Opinion of the International Searching Authority, or the Declaration dated Apr. 2, 2008. Issued in corresponding International Application No. PCT/US2007/083617.

Guillonneau, B. et al. "Laparoscopic Radical Prostatectomy," Computer Motion, Jan. 2000, pp. 1-12, Santa Barbara, CA.

Lieurance, R.K. et al. "Arthroscopic Knot Tying," [online] [retrieved on Sep. 6, 2006]. Retrieved from the Internet: <URL: http://orthonet.on.ca/shoulderscope/arthroscopic_knot_tying.htm>, 7 pages.

Lecture "Human Gross Anatomy and Embryology Pelvic Organs and Pelvic Diaphragm" by Dr. Roberts, University of Minnesota Medical School. Lecture given Fall 2000. Information posted to the internet before Oct. 17, 2000. Describes pelvic floor area.

GyneFlex™—Instructions: Female Pelvic Floor Muscles. Shows color diagrams of the pelvic floor area. Printed Feb. 7, 2003.

"Physicians/Plastic Surgery/Pelvic Floor Dysfunction", Abington Memorial Hospital. Printed Feb. 6, 2003. Describe what the pelvic area constitutes.

International Search Report for International Application No. PCT/US03/18486, dated Jan. 27, 2004.

Capio CL Transvaginal Suture Capturing Device Product Brochure: "Transvaginal Suture Fixation to Cooper's Ligament for Sling Procedure", Boston Scientific Corporation, 2000, pp. 1-4.

Capio Suture Capturing Device Product Brochure: "Reach, Throw and Capture: One Step. One Device", Boston Scientific Corporation, 1998, pp. 1-4.

* cited by examiner

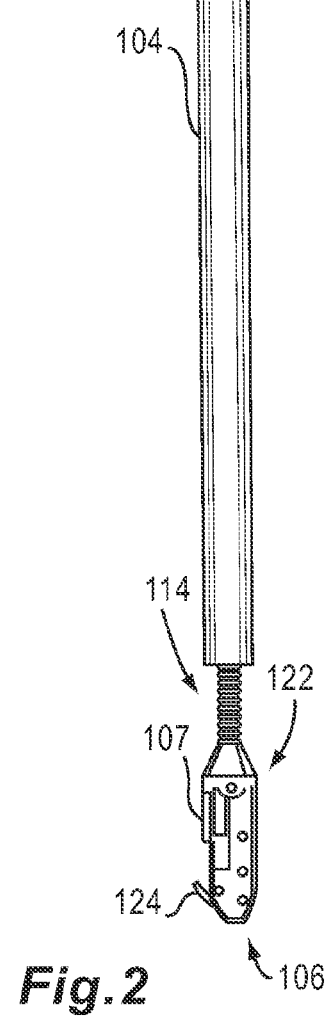
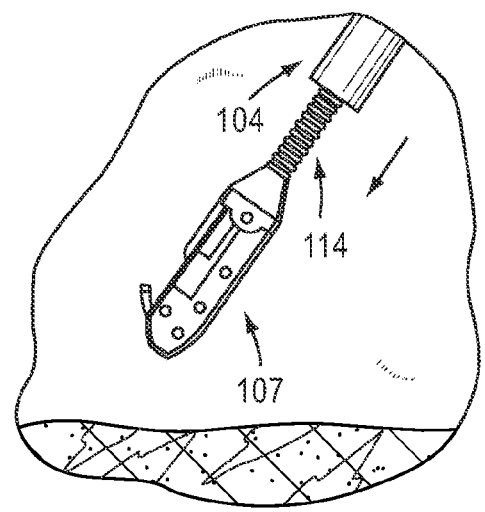
Fig.3A
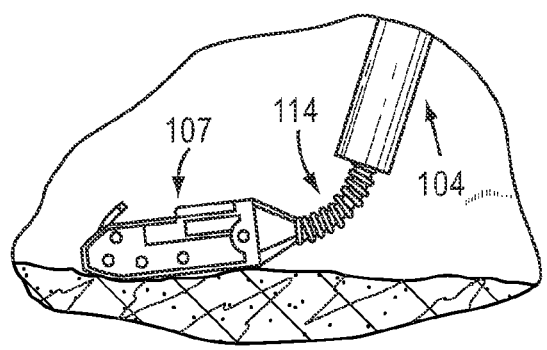
Fig.3B
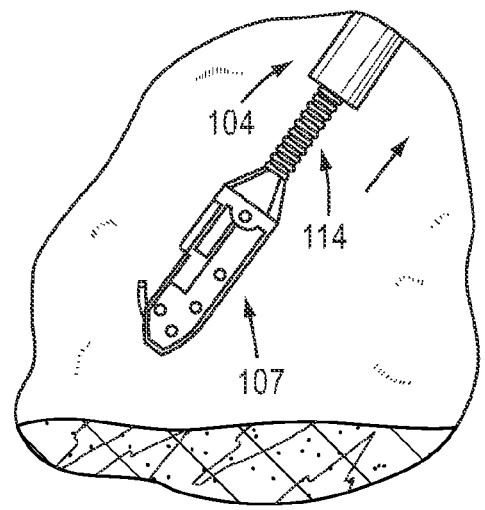
Fig.3C
Fig.2

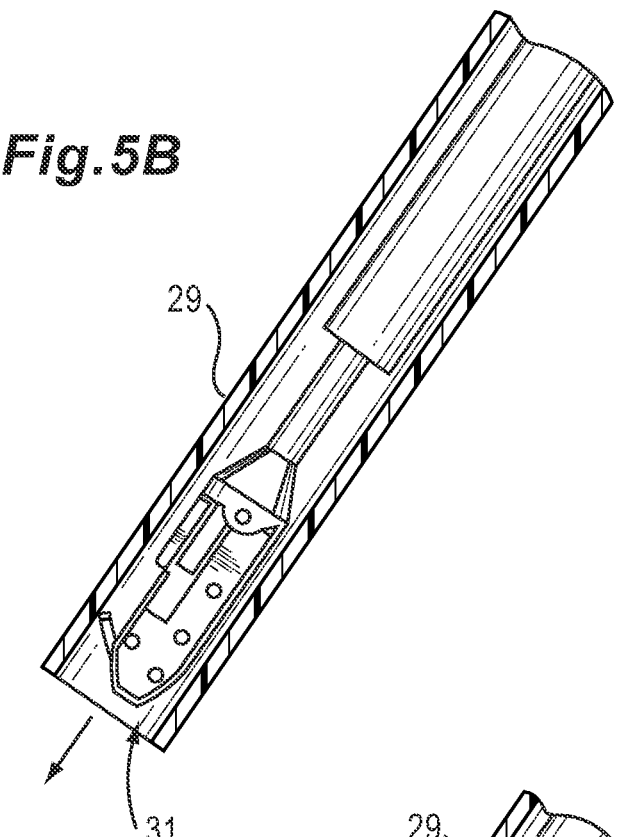
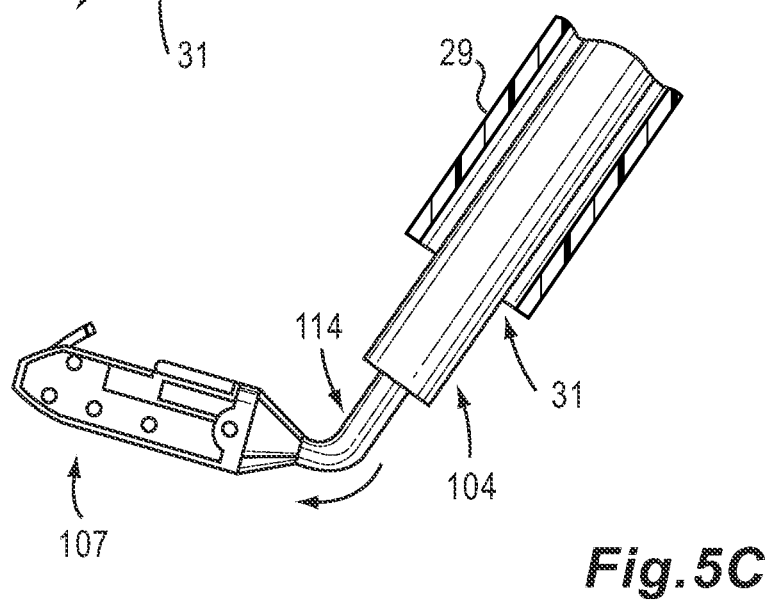

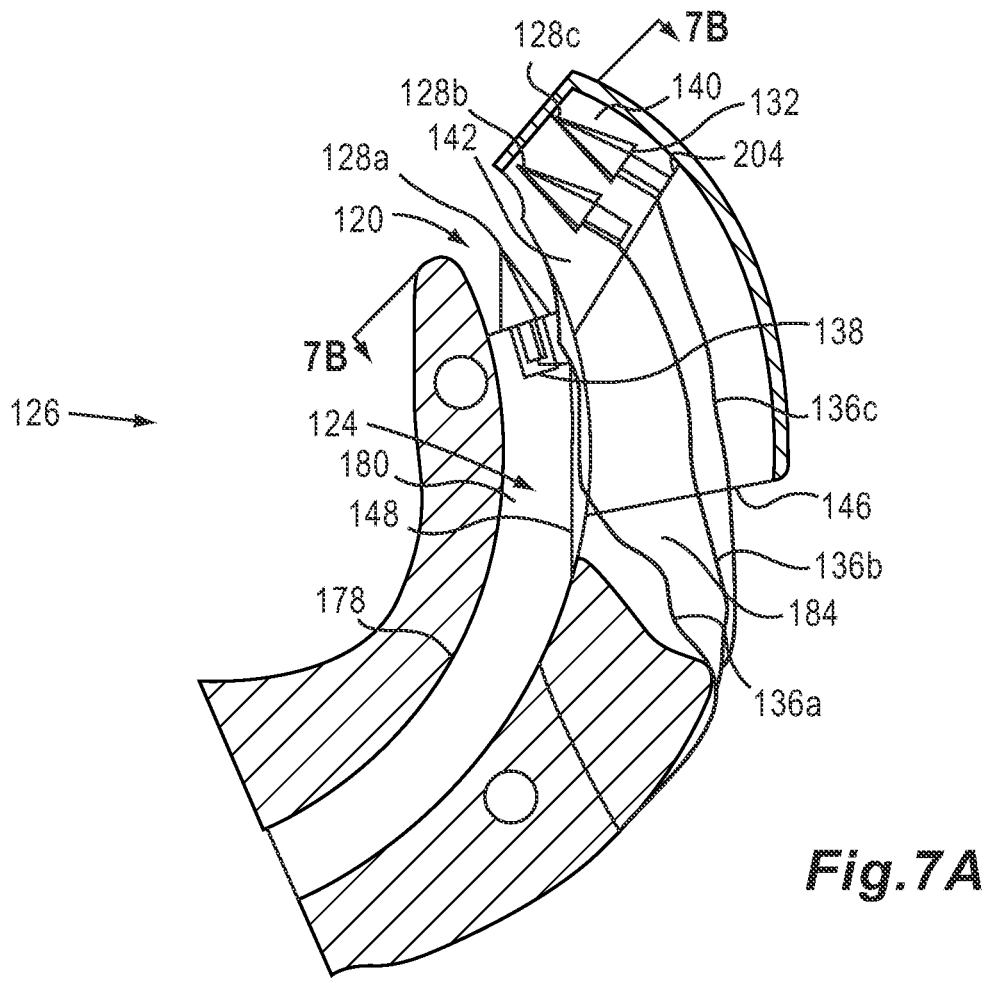
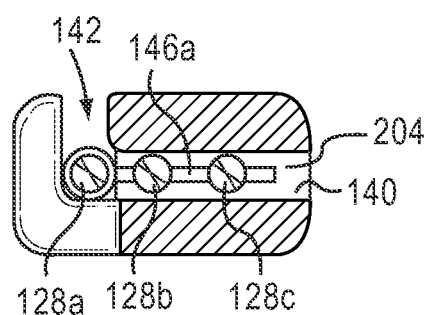
Fig.7A
Fig.7B

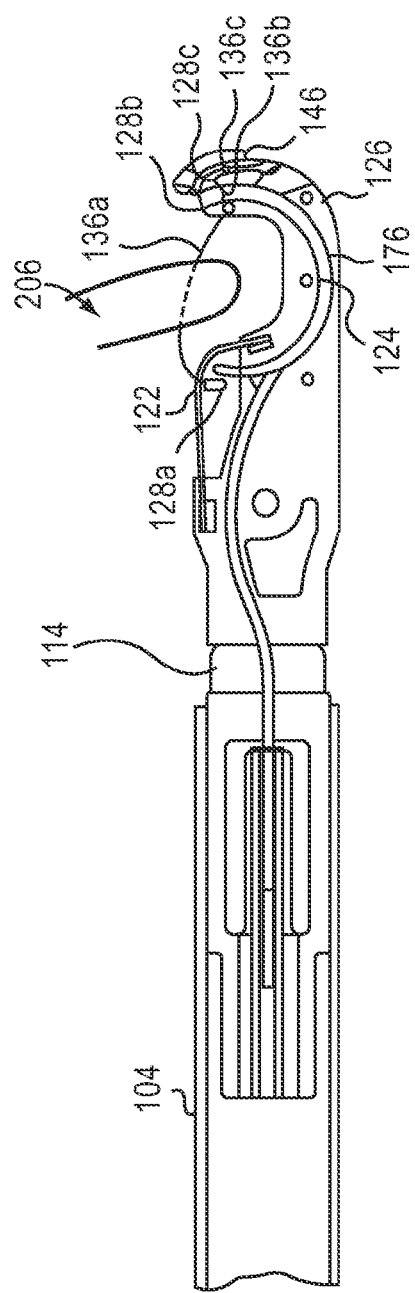
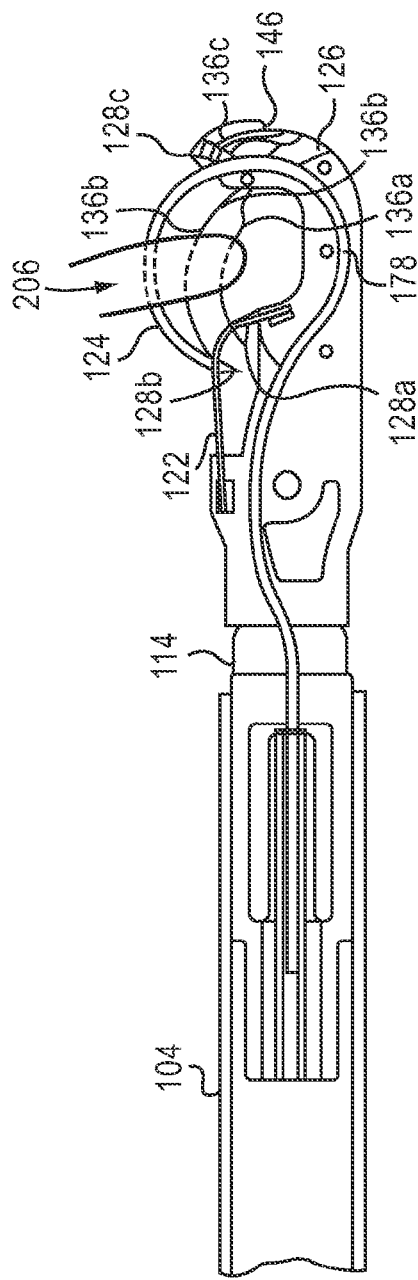

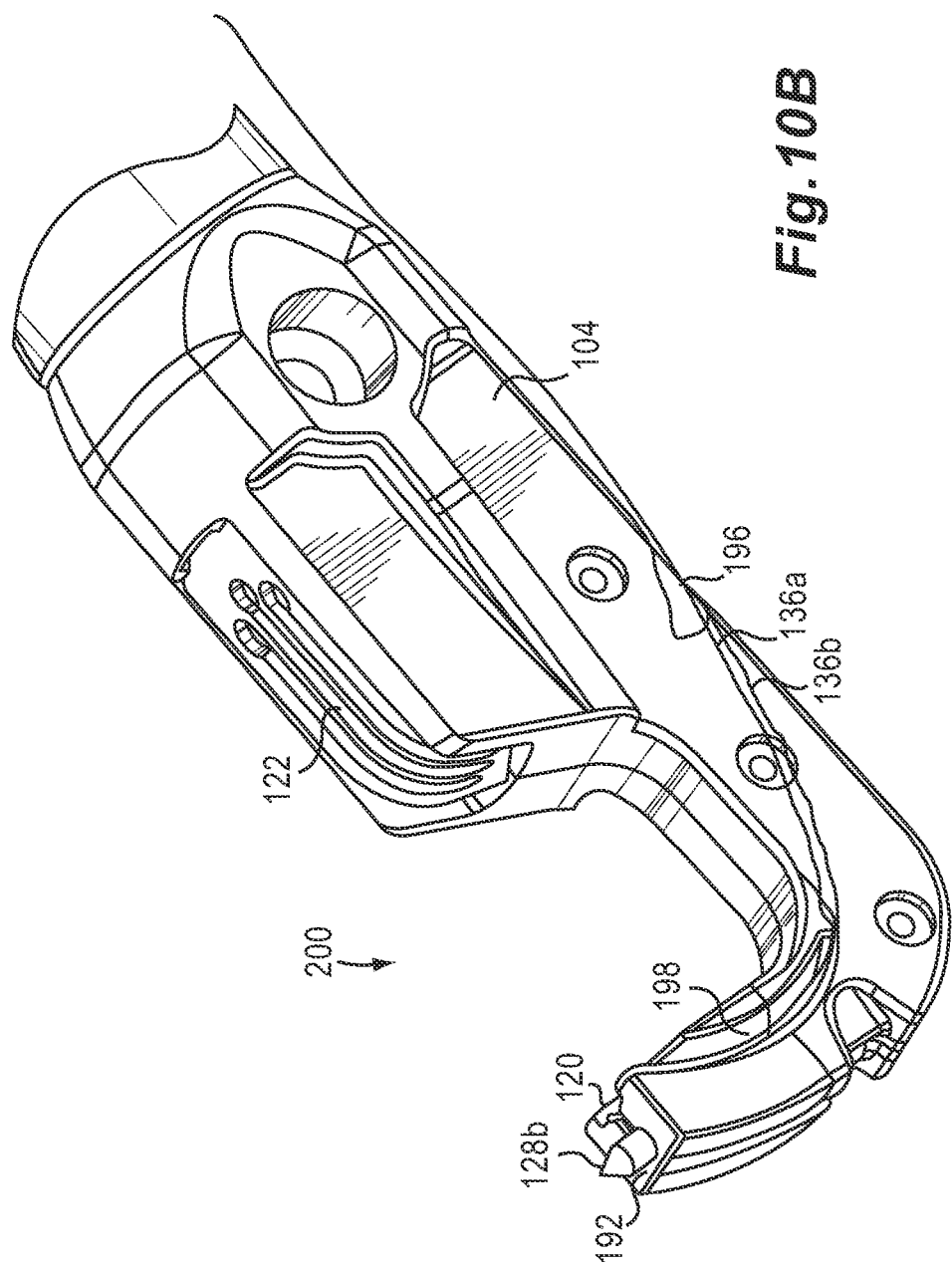

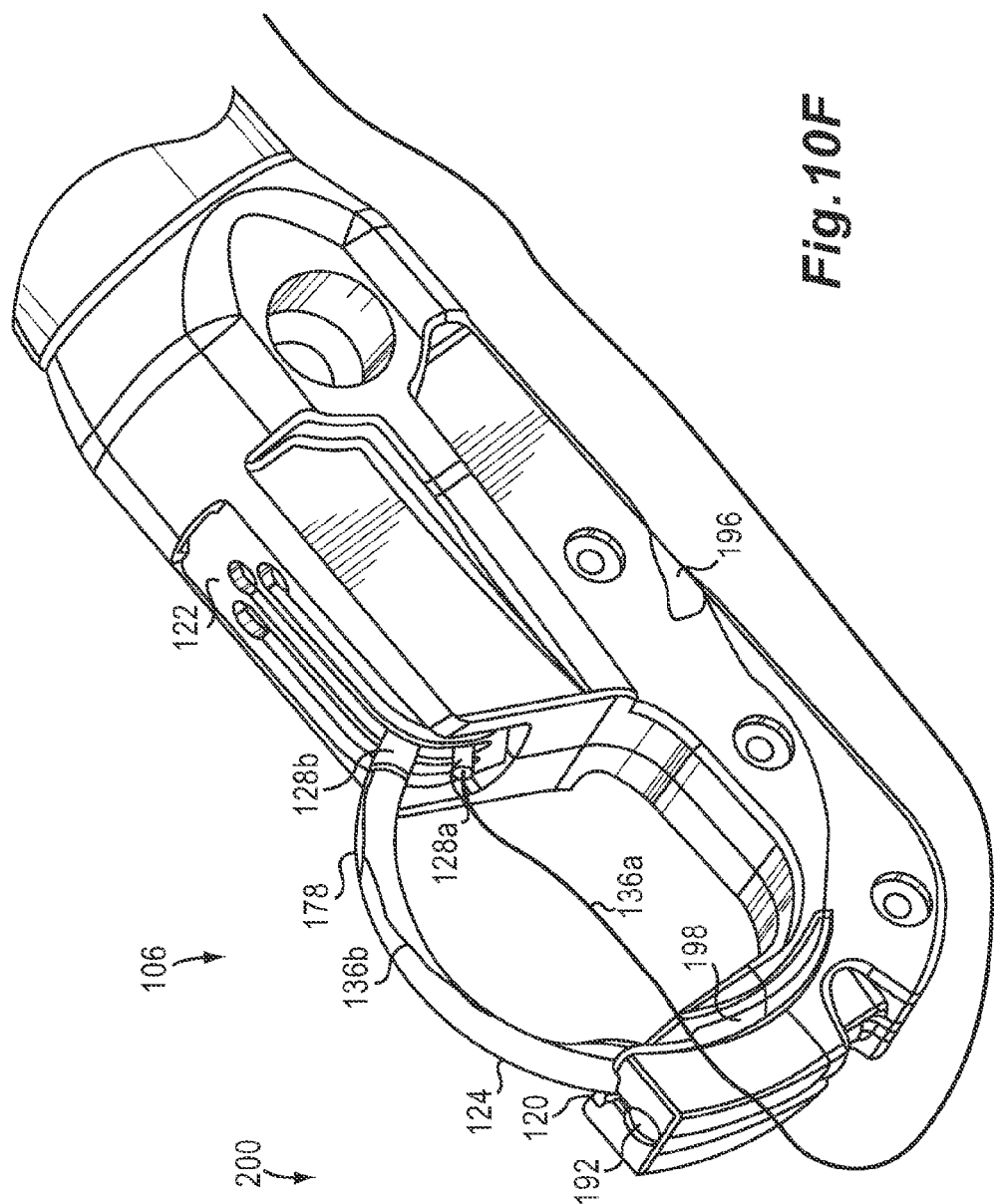

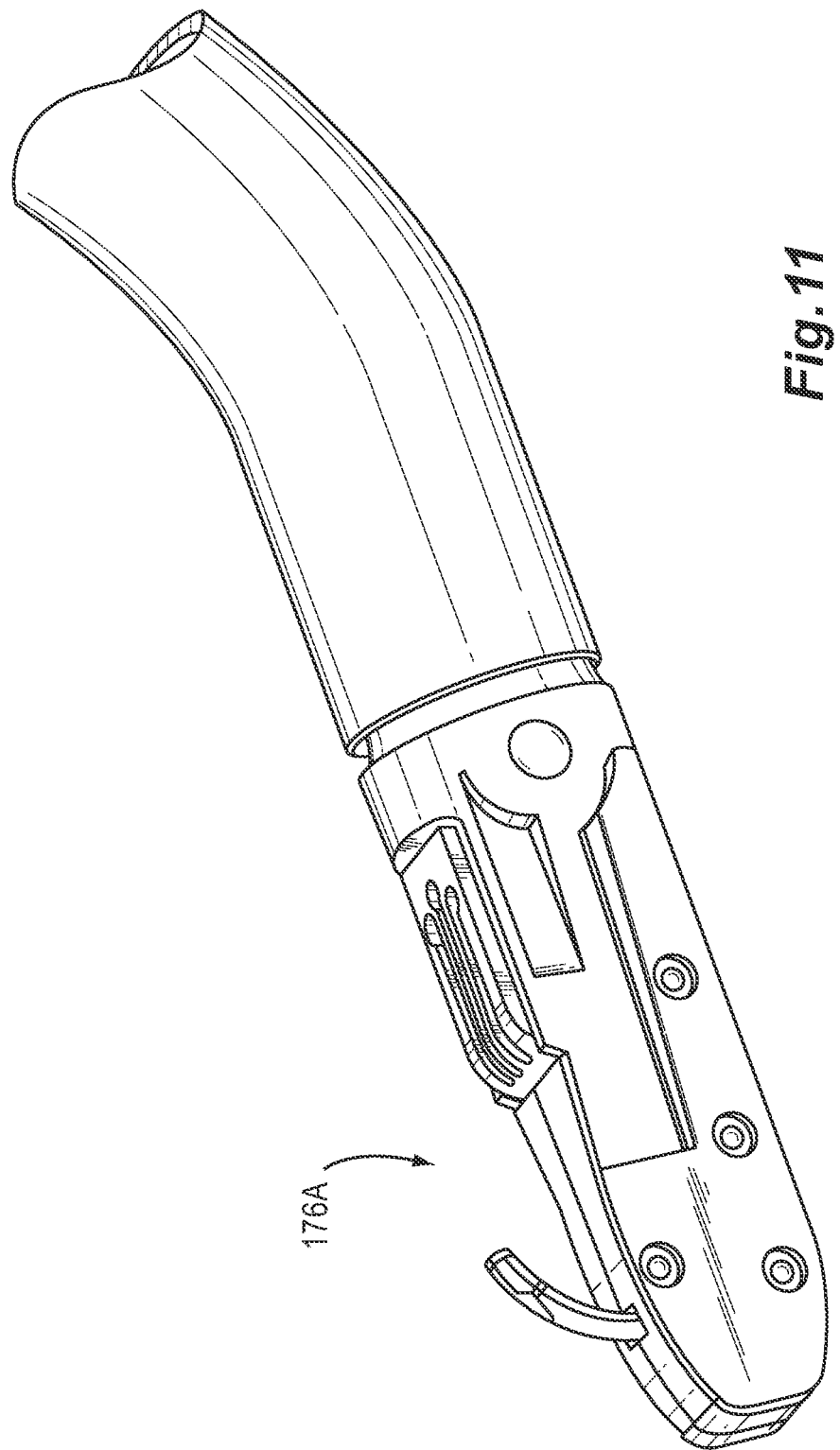

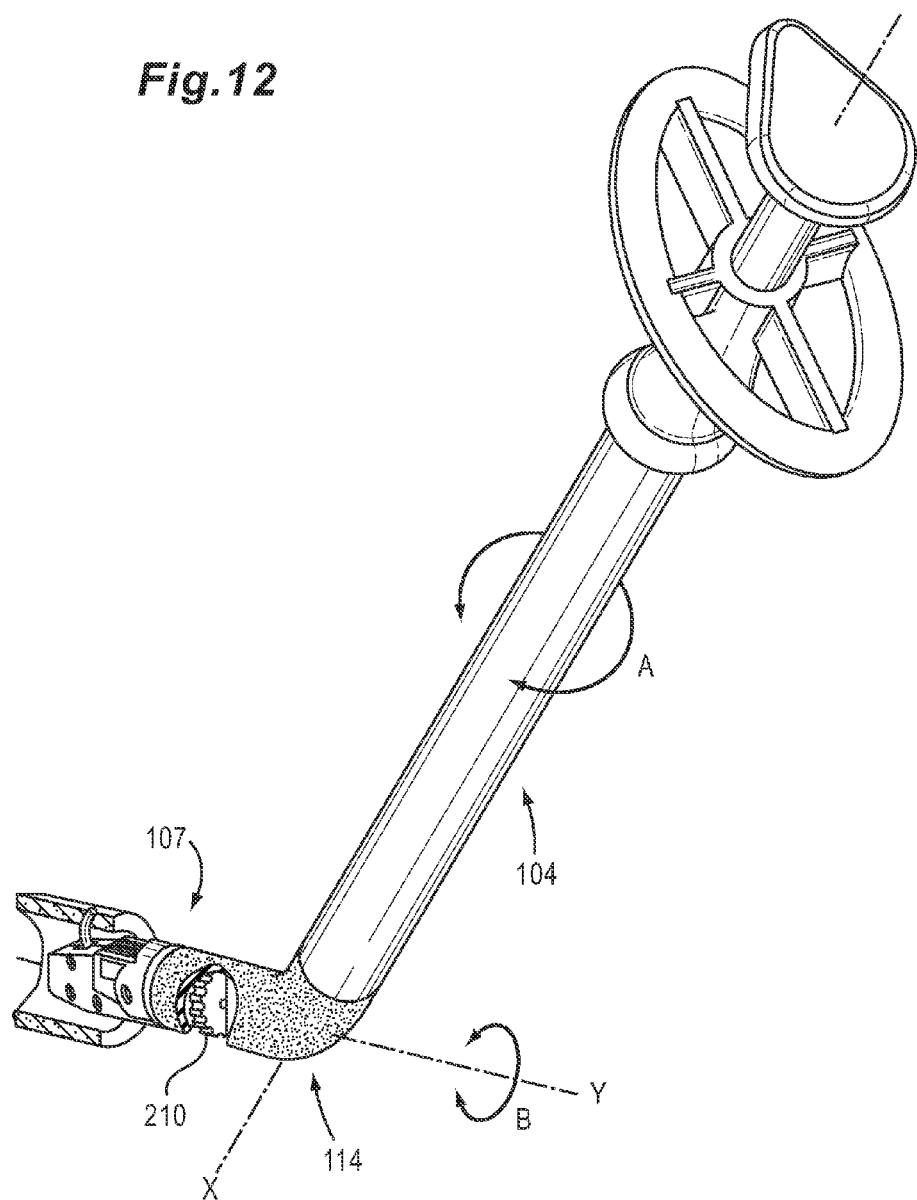

SUTURING INSTRUMENT

This application claims priority to U.S. Provisional Patent Application No. 60/857,615, filed Nov. 7, 2006, entitled "Delivering Sutures," the entire content of which is hereby incorporated by reference.

TECHNICAL FIELD

The invention generally relates to placing sutures. Embodiments according to the invention can be used to navigate tortuous pathways for the purpose of accessing difficult-to-reach treatment areas within the body of a patient.

BACKGROUND INFORMATION

Suturing body tissue is a time consuming aspect of many surgical procedures. For many surgical procedures, it is necessary to make a large opening in the human body to expose the area that requires surgical repair. There are instruments available, such as endoscopes, that allow viewing of certain areas of the human body through a small puncture wound without exposing the entire body cavity. Endoscopes can be used in conjunction with specialized surgical instruments to detect, diagnose, and repair areas of the body that previously required open surgery to access.

Some surgical instruments used in endoscopic procedures are limited by the manner in which they access the areas of the human body in need of repair. In particular, the instruments may not be able to access tissue or organs located deep within the body or that are in some way obstructed. Also, many of the instruments are limited by the way they grasp tissue, apply a suture, or recapture a needle and suture. Furthermore, many of the instruments are complicated and expensive to produce due to the numerous parts and/or subassemblies required to make them function properly.

Suturing instruments, and more specifically suturing instruments used in endoscopic procedures, are generally rigid and do not provide the operator a range of motion to access difficult-to-reach parts of the anatomical region requiring sutures. Accordingly, multiple instruments of various configurations and sizes typically are used to access all of the necessary tissue areas. These limitations of known suturing instruments complicate the endoscopic procedure for the surgeon by requiring the insertion and removal of multiple instruments from a surgical site as the target suturing area changes during the course of the surgical procedure.

SUMMARY OF THE INVENTION

The invention generally relates to suturing instruments with improved maneuverability, efficiency, and functionality for use during a surgical procedure such as an endoscopic or laparoscopic procedure. The disclosed embodiments are directed toward a suturing instrument capable of delivering a suture to a treatment area wherein the treatment area is located in a difficult-to-reach area within the body of a patient. Various medical procedures require a substantially linear instrument in order to reach the treatment area and a non-linear instrument once the instrument reaches the treatment area. For example, the body of the instrument must be fairly linear in order to fit through the cannula of a trocar assembly. The transformation from a substantially linear instrument to a non-linear instrument can be achieved with, for example, an instrument including a head that can be positioned straight or at an angle relative to the shaft of the instrument.

Some illustrative embodiments according to the invention are directed towards a suturing instrument including a suturing head that is coupled to the shaft of an elongate body member by a connector member which may be biased in either a linear orientation along the longitudinal axis of the shaft or any one of a variety of non-linear orientations with respect to the shaft's longitudinal axis. The elongate body member can include a handle at a proximal portion that is engaged to a suturing head at a distal portion by a connector member, the suturing head including a needle carrier and a needle catch. The connector member can comprise a resilient material such that an external force may be applied to the suturing head and move the suturing head from a biased orientation (e.g., linear) to an unbiased orientation (e.g., non-linear). Once the external force is removed, the resiliency of the connector member allows the suturing head to return from the unbiased orientation to the biased orientation. Therefore, a user may adjust the shape of the instrument by applying or removing an external force on the suturing head, such as, for example, pressing the suturing head against the pelvic floor, or placing the suturing head and connector member within the confines of a cannula. An embodiment also comprises a needle partially disposed within a needle carrier, with a suture attached on one end and a tissue-penetrating tip on the other end. An actuator can be used to deliver the needle from the needle carrier to the needle catch. In another embodiment, the suturing instrument can hold and deploy a plurality of suturing needles. In a further embodiment, each suturing needle can be attached to a distinct suture, thereby allowing for the placement of a plurality of sutures prior to removal of the suturing device. The suturing head can define a recess of its surface adjacent to the concave side of the needle carrier. Alternatively, the suturing head does not define such a recess, remaining relatively flat on the surface adjacent to the concave side of the needle carrier to improve its suturing performance in certain circumstances. One such circumstance can include the anastomosis of a lumen (such as a urethra) in which the suturing head is disposed within the lumen, and the suturing needle traverses from the inside to the outside wall of the lumen.

In one embodiment, the connector member can comprise a spring or a plurality of springs, the spring being either in linear orientation or in a pre-formed non-linear or 'bent' orientation. In another embodiment, the connector member can be constructed of a polymer or a flexible plastic.

In an embodiment, the elongate body, connector member and suturing head of the suturing instrument can fit and move rotationally and slidably within a cannula. The cannula can comprise, for example, a laparoscopic trocar assembly.

A further embodiment allows the suturing head to be movable independently of the elongate body member in response to an external force. The connector member in this embodiment can comprise a spring or a plurality of springs, or a flexible polymer or plastic material. The elongate body, connector member and suturing head can be slidably disposed within a cannula. The suturing instrument can include a handle at the proximal portion of the elongate member.

In another embodiment, the suturing instrument can comprise an elongate body member coupled to a suturing head by a flexible connector member, the flexible connector member being biased such that the elongate body member is in a non-linear orientation with respect to the suturing head. The suturing head can be aligned with the elongate body member by an externally applied force, such as when it is placed within a cannula. The flexible connector can comprise a spring or a plurality of springs, or a flexible polymer or plastic.

BRIEF DESCRIPTION OF THE DRAWINGS

The disclosed embodiments will be further explained with reference to the attached drawings, wherein like structures are referred to by like numerals throughout the several views. The drawings are not necessarily to scale, the emphasis having instead been generally placed upon illustrating the principles of the invention and the disclosed embodiments.

FIG. 2 is an embodiment of the presently disclosed suturing instrument;

FIG. 3A shows the suturing instrument of FIG. 2 traveling to a treatment area.

FIG. 3B shows the suturing instrument of FIG. 2 engaging the treatment area. FIG. 3C shows the suturing instrument of FIG. 2 being removed from the treatment area;

FIG. 5B shows the suturing instrument of FIG. 5A being delivered to a treatment area wherein the instrument has been surrounded by a cannula from, for example, a trocar assembly. FIG. 5C shows the suturing instrument of FIG. 5A wherein the suturing head exits the cannula at the treatment area and thereby regains the initial non-linear orientation with respect to the elongate body member;

FIG. 7A is an enlarged cross-sectional view of the distal portion of the suturing instrument of FIG. 1A;

FIG. 7B is a schematic top view of the suturing instrument of FIG. 7A taken at line 7B-7B;

FIGS. 9A-9E are partial schematic cross-sectional views of the distal portion of the suturing instrument of FIG. 1A during various operational phases;

FIGS. 10B-10F are partial schematic perspective views of the distal portion of the suturing instrument of FIG. 9A.

FIG. 11 is a 3-dimensional view of a suturing head of an instrument in which the suturing head does not define a recess adjacent to the inside arc of the needle carrier. This embodiment is useful, for example, in the anastomosis procedure depicted in FIGS. 12-15.

FIG. 12 is a 3-dimensional perspective view of a suturing instrument (such as the instrument of FIG. 11) with the suturing head angled with respect to the long axis of the instrument and inserted into the lumen of a body structure (such as a urethra).

DESCRIPTION

Illustrative embodiments according to the invention are directed towards a suturing instrument including a suturing head that is coupled to the shaft of an elongate body member of the instrument by a connector member which may be biased in either a linear orientation along the longitudinal axis of the shaft or any one of a variety of non-linear orientations with respect to the shaft's longitudinal axis. The connector member can comprise a resilient material such that an external force may be applied to the suturing head and move the suturing head from a biased orientation (e.g., linear) to an unbiased orientation (e.g., non-linear). Once the external force is removed, the resiliency of the connector member allows the suturing head to return from the unbiased orientation to the biased orientation. Therefore, a user may adjust the shape of the instrument by applying or removing an external force on the suturing head.

As will be discussed below, the external force may be supplied by an operator (such as a surgeon or other medical professional) manipulating the shaft of the instrument, or more typically a handle connected to the shaft, to cause the suturing head to contact a treatment area within the body of a patient. The operator then applies a force that causes the connector member to give and the head to deflect. Alternatively, the external force may be applied to the suturing head by surrounding the instrument with the cannula of a trocar assembly. Any one of a wide range of external forces may be used to adjust the position and orientation of the suturing head.

By relying on an external force to adjust the suturing head as opposed to mechanically adjusting the suturing head directly (see, for example, co-owned U.S. Pat. No. 6,955,643 issued Oct. 18, 2005, and U.S. Pat. No. 6,936,054 issued Aug. 30, 2005, and co-owned pending U.S. patent application Ser. No. 11/136,805, filed on May 24, 2005, the entirety of each of which are incorporated herein by reference), the suturing head may more easily travel a tortuous pathway to a treatment area because the head will deflect when coming into contact with tissue on the way to the treatment area. As such, the presently disclosed embodiments may lead to reduced tissue damage. In addition, the presently disclosed embodiments are easier and less expensive to construct as compared to a suturing instrument wherein movement of the suturing head is controlled by mechanically coupling the suturing head to a handle of the instrument.

Figure 1A:
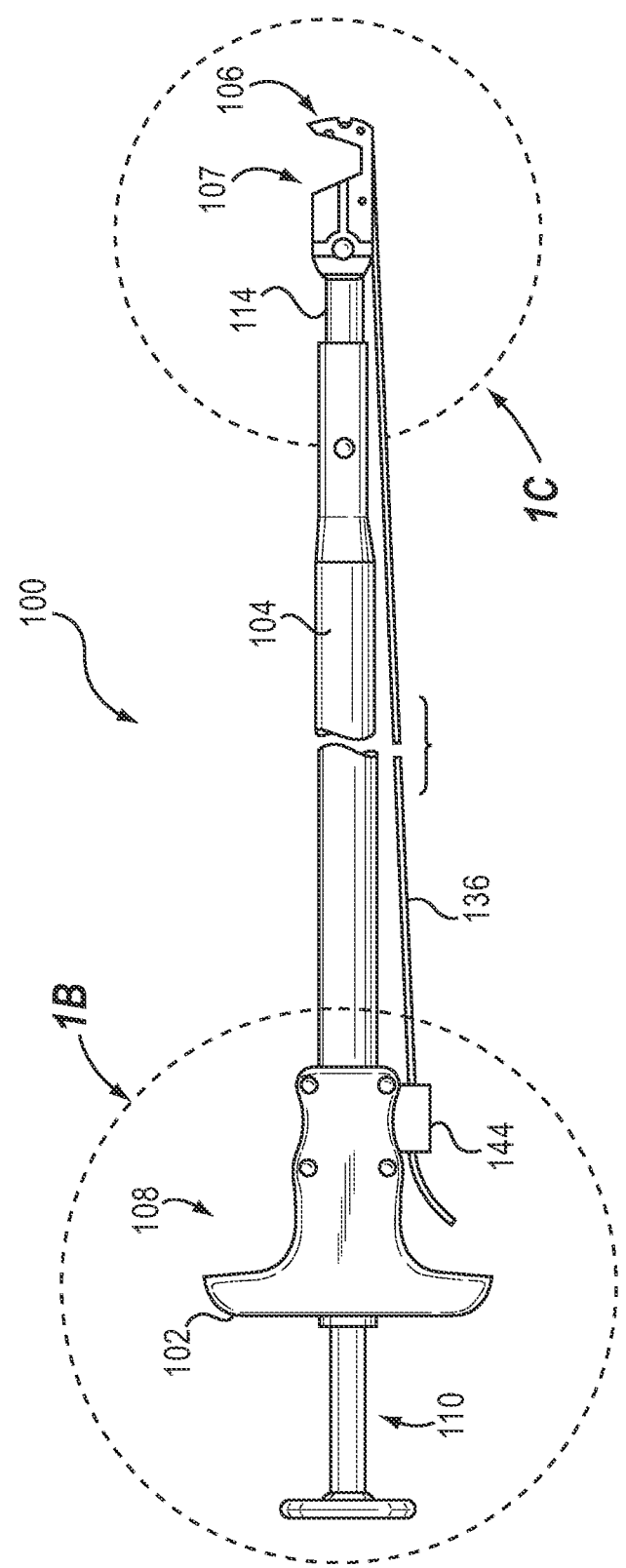
FIG. 1A is a schematic plan view of one embodiment of a suturing instrument in accordance with the invention.

FIG. 1A depicts a presently disclosed embodiment of a suturing instrument 100 including a handle 102, an elongate body member 104, and a needle deployment mechanism 110. The suturing instrument 100 also includes a distal portion 106 and a proximal portion 108. A suturing head 107 is located at the distal portion 106. The various components of the suturing head 107 will be discussed in detail below. The elongate body member 104 is mechanically coupled to the handle 102 at the proximal portion 108 and the suturing components are at least partially disposed within the suturing head 107 of the suturing instrument 100. The suturing instrument 100 comprises a connector member 114 which allows the suturing head 107 to move independently of the elongate body member 104.

The handle 102 could take a variety of forms, for example, the handle 102 could be one of the types used with Boston Scientific Corporation suturing systems, in particular the Capio® Push & Catch suturing system. Generally, the needle deployment mechanism 110 extends longitudinally through the elongate body member 104 to the distal portion 106 of the suturing instrument 100, where the needle deployment mechanism 110 is coupled to a needle 128 (FIG. 7A). The needle deployment mechanism 110 moves the needle 128 between a retracted position and a deployed position. The needle deployment mechanism 110 is shown in greater detail in FIGS. 1B and 1C.

Figure 1B:
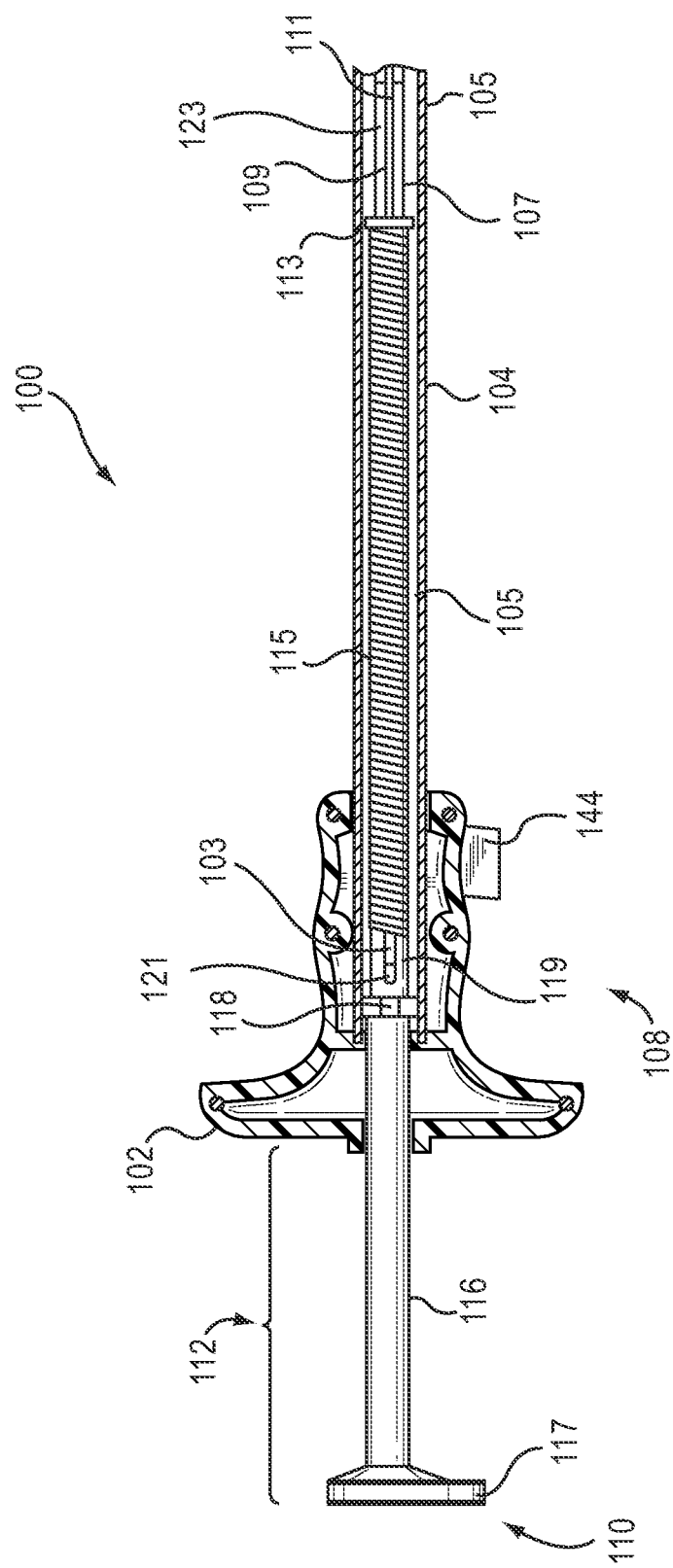
FIGS. 1B and 1C are schematic cross-sectional views of a proximal portion and a distal portion of the suturing instrument of FIG. 1A.

Referring to FIG. 1B, the proximal portion 108 of the suturing instrument 100 includes the handle 102, the elongate body member 104, a suture clip 144, and the needle deployment mechanism 110. The suture clip 144 may be coupled to the handle 102 or the elongate body member 104 and is used to hold an end of one or more sutures prior to placement in a patient. The needle deployment mechanism 110 includes an actuator 112 (button 117, shaft 116), a bearing 118, a button end 119, and a hole 121. The bearing 118 rides along a cylindrical surface 105 that is formed by the inside diameter of the elongate body member 104. A wireform 103 is inserted into the hole 121, coupling it to the actuator button 117. A spring 115 encircles the wireform 103, abuts the button end 119, and is compressed between the button end 119 and a spring washer 113. The spring washer 113 is seated upon a center tube 107. The center tube 107 is housed by the cylindrical surface 105 and is constrained in the distal portion 106. A pusher wire 111 is attached to the wireform 103 by means of a weld, a coupling, adhesive or other means, and is slidably disposed within a guidance sleeve 109, the sleeve 109 being disposed within a cylindrical surface 123 formed by the inside diameter of the center tube 107. In one embodiment, the pusher wire 111 is constructed of nitinol, so chosen for its combination of properties that allow for bendability and high column strength when constrained. Nitinol is a nickel-titanium alloy. Those skilled in the art will recognize that the wire may comprise various materials; these materials are all within the spirit and scope of the present invention.

Figure 1C:
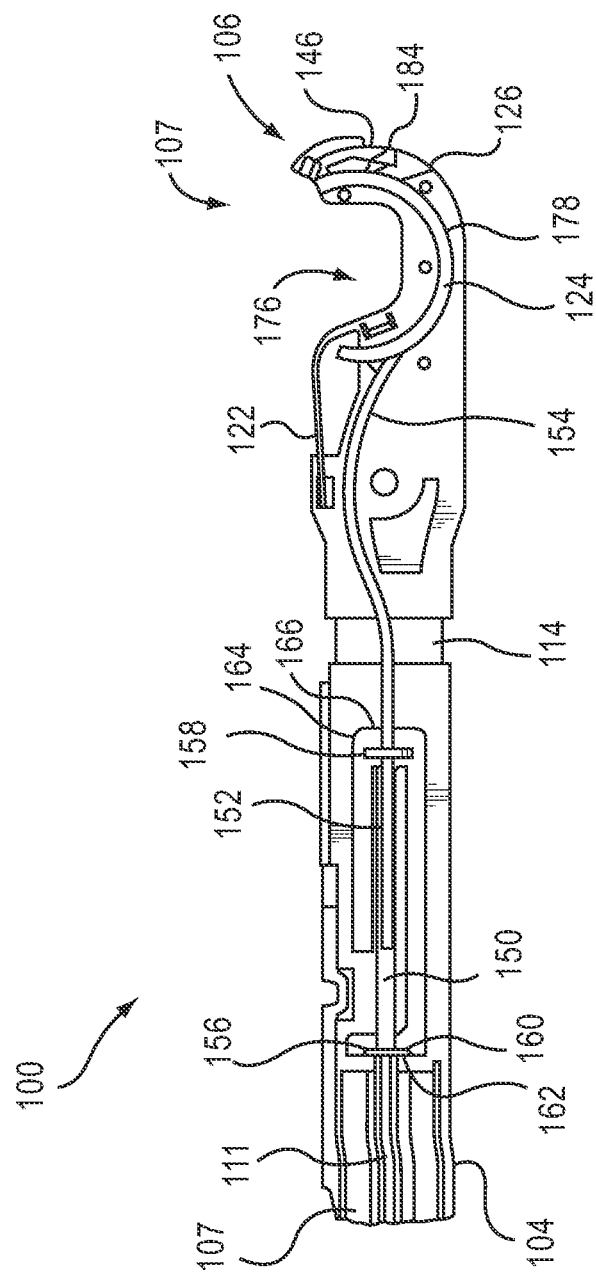
Figure 4:
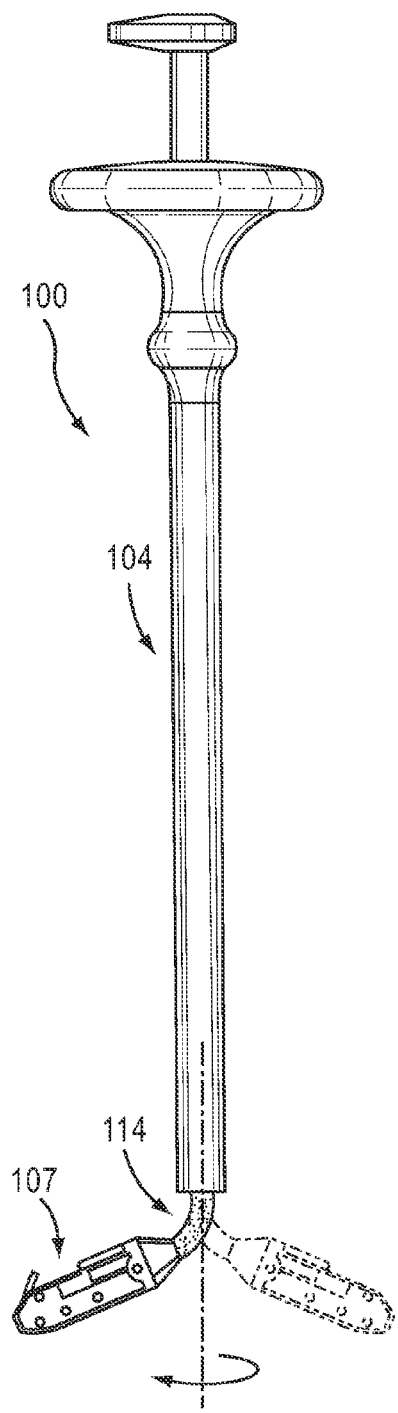
FIG. 4 shows an embodiment wherein the suturing instrument is rotated about an axis of an elongate body member.

Referring to FIG. 1C, the suturing head 107 of the suturing instrument 100 of FIG. 1A includes the elongate body member 104, the needle deployment mechanism 110, a connector member 114, a curved portion 126, and a needle catch 122. Referring again to the needle deployment mechanism 110, the pusher wire 111 is attached by welding or other means to a coupling 150, which is slidably disposed within a track 152. The coupling 150 is attached to a carrier wire 154, which by virtue of its attachment to the coupling 150 is also slidably disposed within the track 152. The carrier wire 154 is mechanically coupled to an extendable needle carrier 124 by means of a weld, a coupling, adhesives, or other means. The coupling 150 abuts a backstop washer 156 that is slidably disposed about the pusher wire 111 and is contained within a pocket 160 that includes a back wall 162, against which the backstop washer 156 rests. The track 152 terminates distally in a pocket 164 that includes a wall 166. A downstop washer 158 is slidably disposed about the carrier wire 154 and constrained within the pocket 164.

Various medical procedures require the suturing instrument 100 to enter the body in a linear or substantially linear shape, assume a non-linear shape once the instrument has reached the treatment area, and subsequently revert to a linear or substantially linear shape prior to being removed from the body. In addition, several medical procedures require an instrument capable of traveling a tortuous pathway with minimal damage to healthy tissue. The presently disclosed suturing instrument 100 comprises a connector member 114 which allows for the suturing instrument 100 to transform from a linear shape to a non-linear shape in response to an external force applied to the suturing head 107 of the suturing device 100. In addition, the presence of the connector member 114 allows for the suturing head 107 to easily deflect when engaging a healthy tissue while traveling to the treatment area.

FIG. 2 shows various aspects of an embodiment of the presently disclosed suturing instrument 100. The suturing instrument 100 comprises an elongate body member 104 wherein the elongate body member 104 comprises a handle 102 at a proximal portion 108. At a distal portion 106, the elongate body member 104 comprises a suturing head 107 engaged to the elongate body member 104 by a connector member 114.

The suturing instrument 100 allows for the suturing head 107 to move independently of the elongate body member 104 by essentially decoupling the suturing head 107 from the elongate body member 104 at the connector member 114. This decoupling allows the suturing head 107 to maintain a linear orientation relative to the elongate body member 104 while the suturing instrument 100 is being delivered to the treatment area and assume a non-linear orientation relative to the elongate body member 104 once the suturing instrument 100 arrives at the treatment area and is subjected to an external force.

In an embodiment, the connector member 114 comprises a flexible spring. In an embodiment, the spring is free to bend in any direction relative to the elongate body member 104. In an embodiment, the spring is covered with a shrink wrap material (or any other suitable material) to prevent matter from entering the suturing instrument 100 through the coils of the spring.

In an embodiment, the connector member 114 comprises a plurality of springs. In an embodiment, each of the plurality of springs comprises a distinct strength and/or stiffness.

In an embodiment, the connector member 114 comprises a flexible inner-tube and a straight outer spring. The inner-tube prevents the nitinol wire from buckling when in compression. The suturing head 107 assumes an angle with respect to the elongate body member 104 when the suturing head 107 is pressed against a treatment area, such as the pelvic floor or inside the urethra.

In an embodiment, the connector member 114 comprises a flexible inner tube and a curved outer spring. The curved outer spring maintains an angled orientation with respect to the elongate body member 104, unless an external force is applied to place the suturing head 107 in a linear orientation with the elongate body member 104. Such an external force can occur, for example, when the suturing head 107, the connector 114 and the elongate body member 104 are confined within a cannula as the suturing instrument 100 is inserted into or withdrawn from a body cavity. When the suturing head 107 is in a linear orientation with the elongate body member 104, rotating the needle deployment mechanism 110 about the axis of the elongate body member 104 of the suturing instrument 100 will cause the suturing head 107 to also rotate about the axis of the elongate body member 104. On the other hand FIG. 12 shows that when the suturing head 107 is in an angled position relative to the elongate body member 104, rotating the needle deployment mechanism 110 in a direction of rotation "A" about the axis "X" of the suturing instrument 100 will cause the suturing head 107 to rotate in a direction of rotation "B" about its own axis "Y". As a result, the suturing head 107 can be made to rotate to a different suturing position while remaining within the lumen of the structure being sutured (such as the urethra), as depicted in FIG. 12.

In an embodiment, the connector member 114 comprises a flexible polymer. In an embodiment, the connector member 114 comprises a flexible plastic. Those skilled in the art will recognize that any resilient material capable of allowing the suturing head 107 to move relative to the elongate body member 104 is within the spirit and scope of the present invention.

FIG. 3A shows an embodiment wherein the suturing instrument 100 is being delivered to a treatment area. In an embodiment, the treatment area is the pelvic floor. As shown in FIG. 7A, the suturing head 107 is substantially linear with respect to the elongate member 104 of the suturing instrument 100 as the suturing instrument 100 navigates a tortuous path to the treatment area. In various medical procedures, a linear device is necessary to reach the treatment area; more specifically, a non-linear device could not navigate the small diameter openings (for example, the cannula of a laparoscopic trocar assembly) through which the suturing instrument 100 needs to travel to reach a desired area. However, once the suturing instrument 100 reaches the treatment area, a non-linear device is required to perform the necessary procedure; i.e., the placement of sutures 136.

FIG. 3B shows the suturing instrument 100 reaching the treatment area (i.e., the pelvic floor). As shown, the suturing head 107 engages the pelvic floor and is pushed against the pelvic floor. As the pelvic floor supplies an external force to the suturing head 107, the suturing head 107 assumes a non-linear orientation with respect to the elongate body member 104. The non-linear orientation is possible because the suturing head 107 is decoupled from the elongate body member 104 at the connector member 114. As discussed above, the connector member 114 comprises a flexible material allowing the suturing head 107 to bend relative to the elongate body member 104 in response to an external force. Once the non-linear orientation is assumed, the suturing instrument 100 is ready to supply sutures 136 to the treatment area (as discussed in detail below).

FIG. 3C shows the removal of the suturing instrument 100 from the treatment area. As the suturing instrument 100 is withdrawn, the external force acting on the suturing head 107 is removed (i.e., the pelvic floor is no longer exerting a force on the suturing head 107). With the removal of this external force, the suturing head 107 resumes the initial linear orientation with respect to the elongate body member 104. The connector member 114 comprises a resilient, flexible material which allows the suturing head 107 to move in all directions relative to the elongate body member 104 in response to an external force; however, the resiliency of the connector member 114 allows the suturing head 107 to resume the initial linear orientation to the elongate body member 104 once the external force is removed. Once the suturing head 107 has resumed a substantially linear orientation with respect to the elongate body member 104, the suturing instrument 100 may be retracted from the treatment area and out of the body.

FIG. 12 shows an embodiment wherein the needle deployment mechanism 110 is rotated in the "A"-direction (as shown by an arrow) about an "X" axis of the elongate body member 104. By rotating inner tube within the elongate body member 104 about the "X"-axis in the direction of arrow "A", the suturing head 107 rotates about an axis "Y" in the direction of arrow "B". The flexible inner tube can be a flexible spring 115 situated within a larger flexible polymer connector member 114. Rotation of the needle deployment mechanism 110 causes rotation of the suturing head 107 about its axis "Y" through the rotation of the flexible inner tube within the connector member 114. A further embodiment shown in FIG. 12 includes a ratchet assembly 210 to maintain the axial orientation suturing head 107 during insertion of the suturing instrument 100 through a cannula. In an embodiment, the suturing head 107 is rotated prior to inserting the instrument 100 into a body.

Figure 5A:
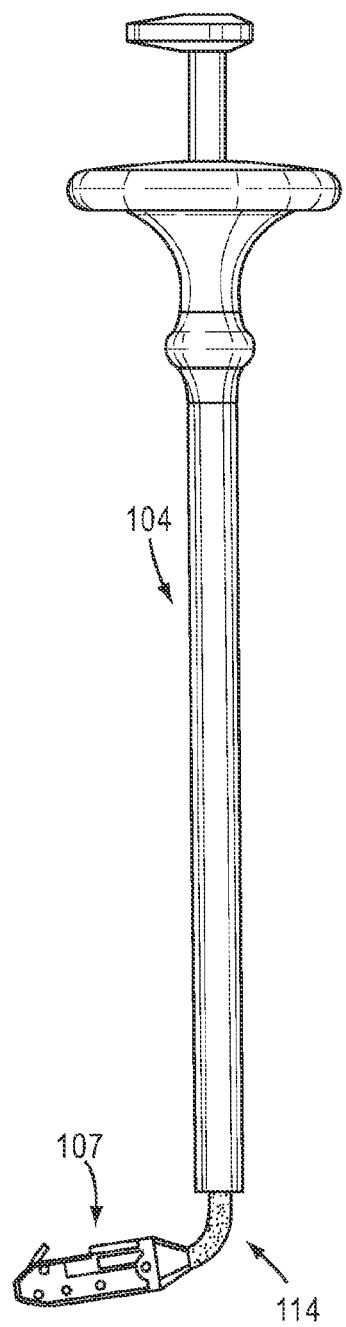
FIG. 5A shows an embodiment of the presently disclosed suturing instrument wherein the suturing head is biased in a non-linear orientation with respect to the elongate body member.

FIG. 5A shows an embodiment wherein the suturing head 107 is biased towards a substantially non-linear orientation with respect to the elongate body member 104 of the suturing instrument 100. The initial non-linear orientation is possible because the connector member 114 is pre-formed at an angle such that in the absence of an exterior force, the suturing head 107 remains in a substantially non-linear orientation with respect to the elongate body member 104.

In an embodiment, the connector member 114 is a pre-formed bent spring. In an embodiment, the connector member 114 comprises a pre-formed polymer. In an embodiment, the connector member 114 comprises a pre-formed plastic. Those of skill in the art will recognize that the connector member 114 may comprise various materials and remain within the spirit and scope of the present invention.

FIG. 5B shows the suturing instrument 100 of FIG. 5A wherein the suturing instrument 100 has been partially surrounded by the cannula 29 of a trocar assembly. (As used herein, a trocar assembly consists of an obturator and a cannula, in which the obturator has a pointed end and can slide within the lumen of the cannula, and can penetrate the skin or wall of an organ, allowing the cannula to be subsequently left in place). The cannula 29 produces an external force on the connector member 114 which substantially straightens the connector member 114 thereby resulting in a substantially linear relationship between the suturing head 107 and the elongate body member 104.

In an embodiment, the cannula 29 comprises a bio-compatible plastic. In an embodiment, the cannula 29 comprises a bio-compatible polymer. In an embodiment, the cannula 29 is a laparoscopic cannula 29. The cannula 29 comprises a material capable of supplying an external force on the suturing instrument 100 which results in a substantially linear relationship between the suturing head 107 and the elongate body member 104 of the suturing instrument 100. Therefore, the suturing instrument 100 surrounded by the cannula 29 may be delivered to the treatment area while maintaining a substantially linear relationship between the suturing head 107 and the elongate body member 104.

Once the cannula 29 reaches the treatment area, the suturing instrument 100 resumes a non-linear orientation by exiting the cannula 29. FIG. 5C shows the suturing instrument 100 exiting the cannula 29 at the distal cannula opening 31. Once the connector member 114 substantially exits the cannula 29, the cannula 29 is no longer supplying an external force on the connector member 114; therefore, the connector member 114 is free to reassume a pre-formed bent configuration wherein the suturing head 107 assumes a non-linear orientation as compared to the elongate body member 104. Once the suturing procedure is complete, the suturing head 107 is withdrawn into the cannula 29 and regains the substantially linear orientation. Once inside the cannula 29, the suturing instrument 100 may be withdrawn from the body.

Figure 6A:
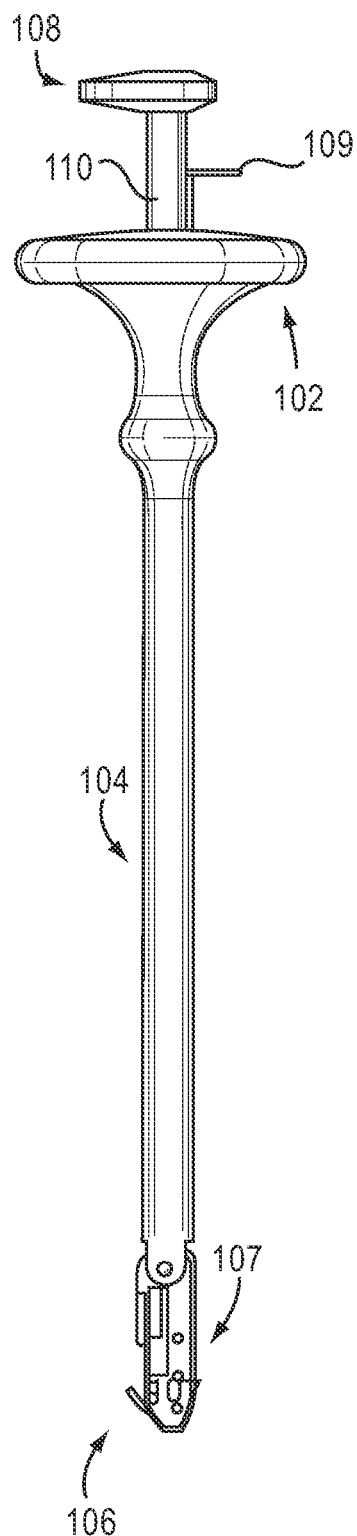
FIG. 6A shows an embodiment of a suturing device wherein the suturing head is engaged to an elongate body member by a hinge pin.
Figure 6B:
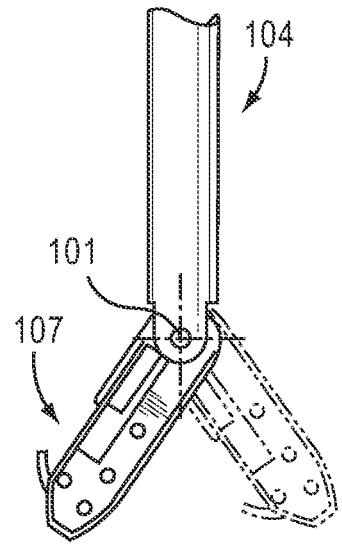
FIG. 6B shows a distal portion of the suturing device of FIG. 6A.
Figure 6C:
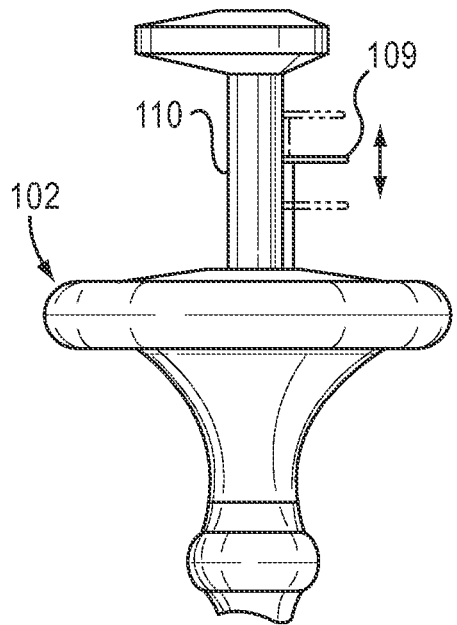
FIG. 6C shows a proximal portion of the suturing device of FIG. 6A.

FIG. 6A shows an embodiment wherein the suturing head 107 is engaged to the elongate body member 104 at a hinge pin 101. The suturing head 107 is engaged to a head adjustment rod 109 which is accessible to a user at the handle 102. FIG. 6B shows a view of the distal portion 106 of the suturing instrument 100. As shown, the suturing head 107 is engaged to the elongate body member 104 at a hinge pin 101. FIG. 6C shows a view of the distal portion 106 of an embodiment of the suturing instrument wherein a head adjustment rod 109 is engaged to the handle 102. In an embodiment, the head adjustment rod 109 is engaged to the suturing head 107; as such, a user may pivot the suturing head 107 about the hinge pin 101 by applying a force to the head adjustment rod 109.

Figure 9A:
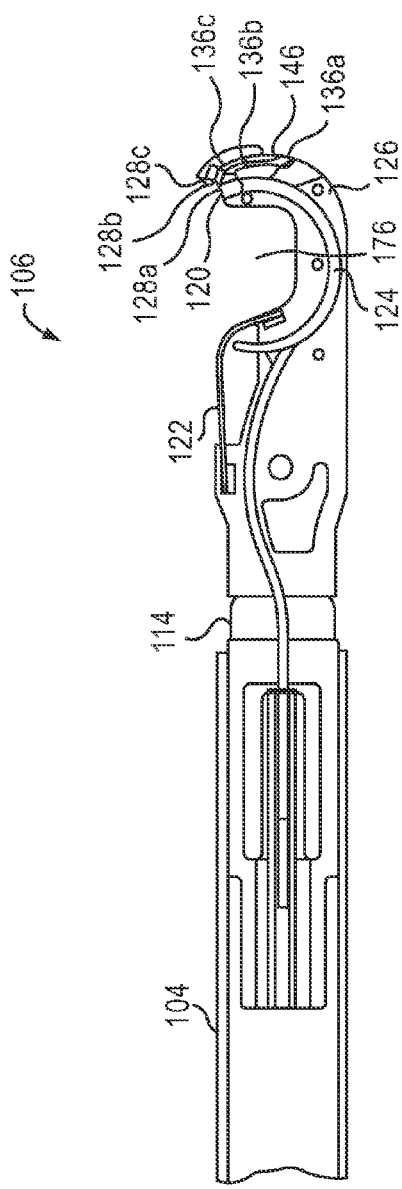

Referring to FIGS. 7A and 7B, the curved portion 126 defines a channel 178, an opening (or needle exit port 120) including a tunnel or (needle compartment 140), a needle input/output slot 142, and a suture slot 146. The curved portion 126 also defines a recess 176 for receiving tissue (FIG. 1C). The curved portion 126 also includes a knot pusher 184. The needle carrier 124 is disposed within the channel 178 in the curved portion 126. A distal portion 180 of the needle carrier 124 defines a lumen 138 for holding a needle 128a, 128b, or 128c (generally needle 128). An alternative embodiment is shown in FIG. 11, in which the suturing head 107 does not define a recess 176 as shown in FIG. 1C and FIG. 9A. Instead, the contour of the suturing head at 176A of FIG. 11 is relatively flat. Absence of the recess 176 helps to prevent the prolapse of tissue inward within the inside arc of the needle carrier 124 when the suturing head 107 is placed within a lumen to suture through the wall of the lumen. The distortion created by the prolapse of tissue could otherwise disturb the proper placement of the needle 128. This design is useful, for example, in the anastomosis of the transected urethra to the urethral orifice of the neck of the bladder during radical prostatectomy surgery, as described later and schematically illustrated in FIGS. 12 to 15.

Figure 8A:
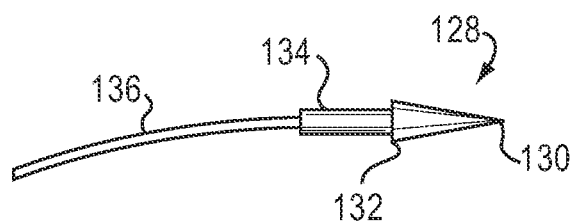
FIG. 8A is a schematic plan view of a needle coupled to a suture for use in a suturing instrument in accordance with the invention.

Referring to FIG. 8A, in one embodiment, the needle 128 includes a tip 130 and a shaft 134 coupled to the tip 130, thereby forming a shoulder 132. The shaft 134 is coupled to a suture 136a, 136b, 136c (generally suture 136). The needle 128 is inserted into the lumen 138 and held by a slight friction fit. The suture 136 extends out of a needle carrier suture slot 148 and the suture slot 146. Needles 128b and 128c are stored in the needle compartment 140 prior to being deployed.

Figure 8B:
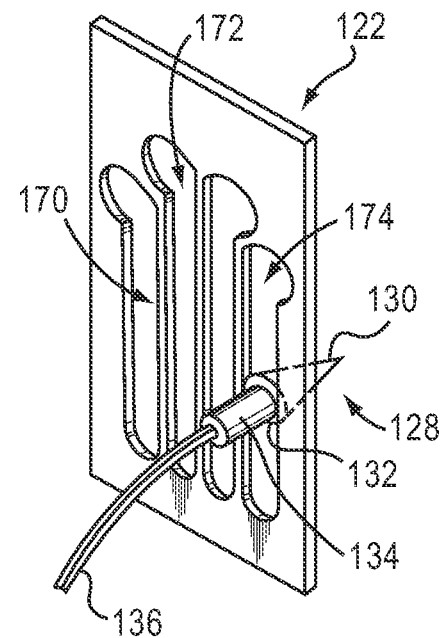
FIG. 8B is a schematic perspective view of a needle catch for use with the suturing instrument of FIG. 1A.

Referring again to FIGS. 1B, 1C, 7A, and 7B, in operation, a user (such as a physician or other medical personnel) actuates the needle deployment mechanism 110 by pushing on the button 117, which via the attachment to the wireform 103 which is attached to the pusher wire 111, moves the coupling 150 along the track 152 concomitantly moving the carrier wire 154, which slidably moves the needle carrier 124 through the needle exit port 120. The user continues to push the button 117 until the needle 128 enters the needle catch 122. The needle catch 122, as shown in FIG. 8B, includes openings 170 defined by successive ribs 172. The needle catch 122 receives the needle 128 (coupled to the suture 136) through opening 170, the ribs 172 deflect slightly to allow the needle 128 to pass through. After the formed shoulder 132 has passed the ribs 172, the ribs 172 spring back to their original position defining the openings 170, and the needle 128 remains captured in the needle catch 122. The user releases the button 117 and the spring 115 urges the button 117 proximally, moving the pusher wire 111, the coupling 150, the carrier wire 154, and the needle carrier 124 proximally along with the button 117 to the retracted position. As the needle carrier 124 moves back to the retracted position, the needle 128 slides out of the lumen 138. The openings 170 are chosen to be smaller in dimension than the formed shoulder 132. This causes the needle catch 122 to retain the needle 128 because the flat rear surface of the shoulder 132 prevents the needle 128 from passing back through the opening 170. When it is necessary to remove the needle 128 from the needle catch 122, the needle 128 may be moved toward an enlarged portion 174 of opening 172. The enlarged portion 174 is sized to allow the formed shoulder 132 to pass through without resistance. The needle catch 122 is preferably constructed of thin stainless steel of high temper, such as ANSI 301 full hard. The needle catch 122 may be fabricated by means of stamping, laser machining, or chemical etching.

The suturing instrument's component materials should be biocompatible. For example, the handle 102, the elongate body member 104, and portions of the needle deployment mechanism 110 may be fabricated from extruded, molded, or machined plastic material(s), such as polypropylene, polycarbonate, or glass-filled polycarbonate. Other components, for example the needle 128, may be made of stainless steel. Other suitable materials will be apparent to those skilled in the art. The material(s) used to form the suture should be biocompatible. The surgeon will select the length, diameter, and characteristics of the suture to suit a particular application. Additionally, the mechanical components and operation are similar in nature to those disclosed in U.S. Pat. Nos. 5,364, 408 and 6,048,351, each of which is incorporated by reference herein in its entirety.

Referring to FIGS. 7A-7B and 9A-9E, the present invention enables a user to place multiple sutures 136 in a patient without removing the suturing instrument 100 from the patient. The user loads the suture 136c through the first suture slot 146a until the suture 136c emerges from the second suture slot 146b. The user then inserts the needle 128c through the needle input/output slot 142 into the needle compartment 140. The user repeats this process for additional sutures 136 and needles 128. The user can repeat this process for loading the first suture 136a and the first needle 128a, or the user can insert the first needle 128a directly into the needle carrier 124. In either case, the sutures 136a, 136b, 136c extend out of the second suture slot 146b. If the needle 128a is loaded into the needle compartment 140, the user pulls on the first suture 136a (held by the suture clip 144) to cause the first needle 128a to slide down an inclined needle shelf 204 and out of the needle compartment 140 through the needle output slot 142 into the lumen 138 of the needle carrier 124. The suture 136a extends out of the needle suture slot 148 and the second suture slot 146b.

In another embodiment, the suture 136a could be pulled by attaching the suture 136a to a spool mounted on the elongate body member 104 and winding the spool. In still other embodiments, the suture 136a could be pulled by other mechanical means known in the art, such as by a lever, for example. After the needles 128a, 128b, 128c and sutures 136a, 136b, 136c are loaded into the suturing instrument 100, portions of the sutures 136a, 136b, 136c extending out the suture slot 146b are held by the suture clip 144 (FIG. 1B). The needle carrier 124, which is part of the needle deployment mechanism 110, is sequentially connectable to the needles 128 stored in the needle compartment 140. This means that each needle 128 stored in the needle compartment 140 is connected to, and then deployed by, the needle carrier 124 one at a time in the order the needles 128 are dispensed from the needle compartment 140.

Figure 9B:
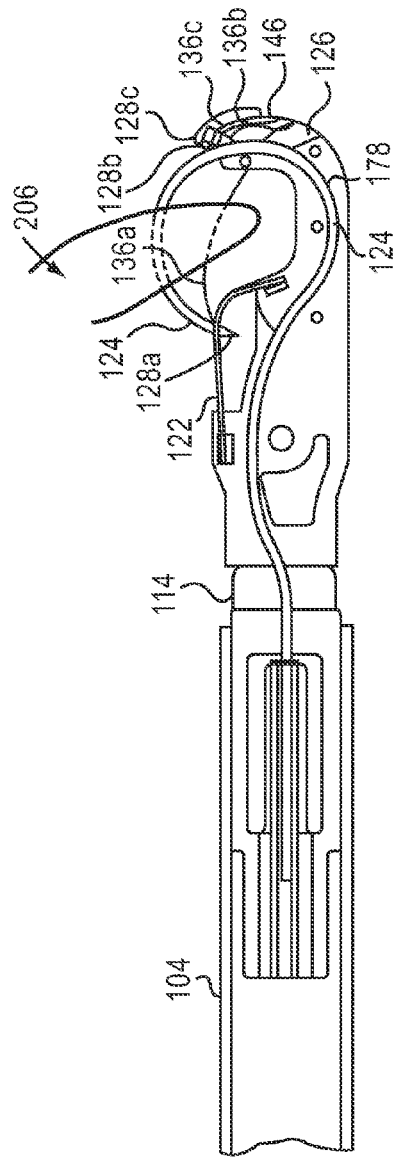

The user then inserts the elongate body member 104 into a patient and orients the elongate body member 104 so that the needle exit port 120 is proximate to or in contact with the tissue 206 to be sutured. The user then pushes the button 117 (FIG. 1B), as described above. Pushing the button 117 causes the needle carrier 124 (holding the first needle 128a) to extend out of the needle exit port 120 and push the needle 128a through the tissue 206. As the first needle 128*a* is pushed through the tissue 206, the first needle 128*a* pulls the first suture 136*a* through the tissue 206. As the user continues to push the button 117, the needle carrier 124 continues to advance out of the needle exit port 120 and directs the first needle 128*a* and the first suture 136*a* toward the needle catch 122. The user continues to push the button 117 until the first needle 128*a* contacts and becomes captured by the needle catch 122 (FIG. 9B). The user then retracts the needle carrier 124 by releasing the button 117, as previously described.

Figure 9E:
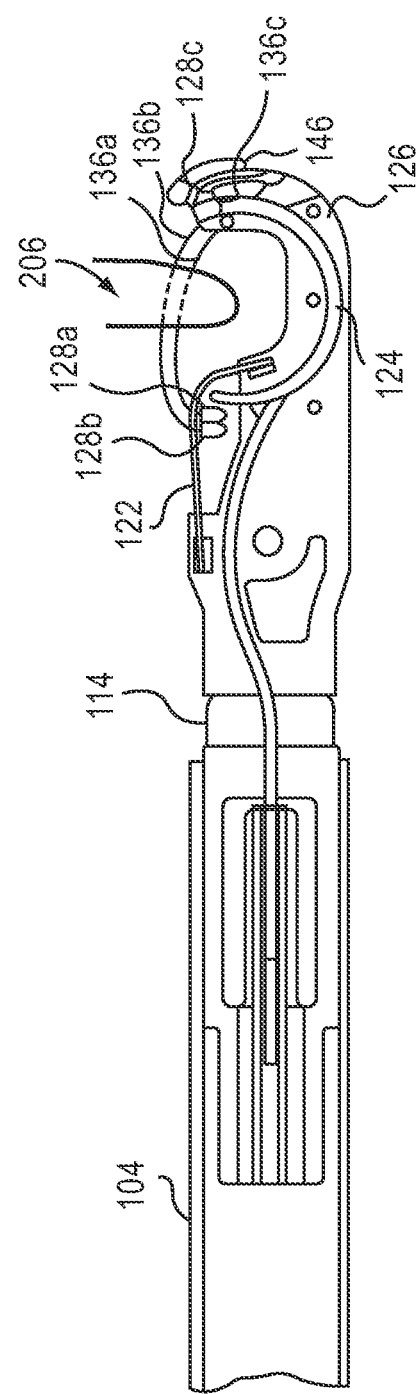

After the user retracts the needle carrier 124, the first needle 128*a* and the first suture 136*a* are left captured within the needle catch 122, with the first suture 136*a* extending through the tissue 206 (FIG. 9C). When the needle carrier 124 returns to a fully retracted position, the user pulls on the second suture 136*b* to cause the second needle 128*b* to slide down the inclined needle shelf 204 and out of the needle compartment 140 through the needle input/output slot 142 and into the lumen 138 of the needle carrier 124. The second suture 136*b* extends out of the needle carrier suture slot 148 and the second suture slot 146*b*. The user then advances the needle carrier 124 as described above until the second needle 128*b* is captured by the needle catch 122 (FIG. 9D). The user then retracts the needle carrier 124 as described above leaving the second needle 128*b* and the second suture 136*b* captured by the needle catch 122 (FIG. 9E). This procedure can be repeated for the third needle 128*c*, or for as many needles as may be stored in the needle compartment 140.

After one or more sutures 136 have been placed, the user withdraws the suturing instrument 100 from the patient. The user detaches the suture(s) 136 from the needle(s) 128 and ties a knot or knots into the suture(s) 136. The user can then use the knot pusher 184 (shown in FIG. 1C) to push the knot(s) into the patient as the knot(s) is tightened.

Figure 10A:
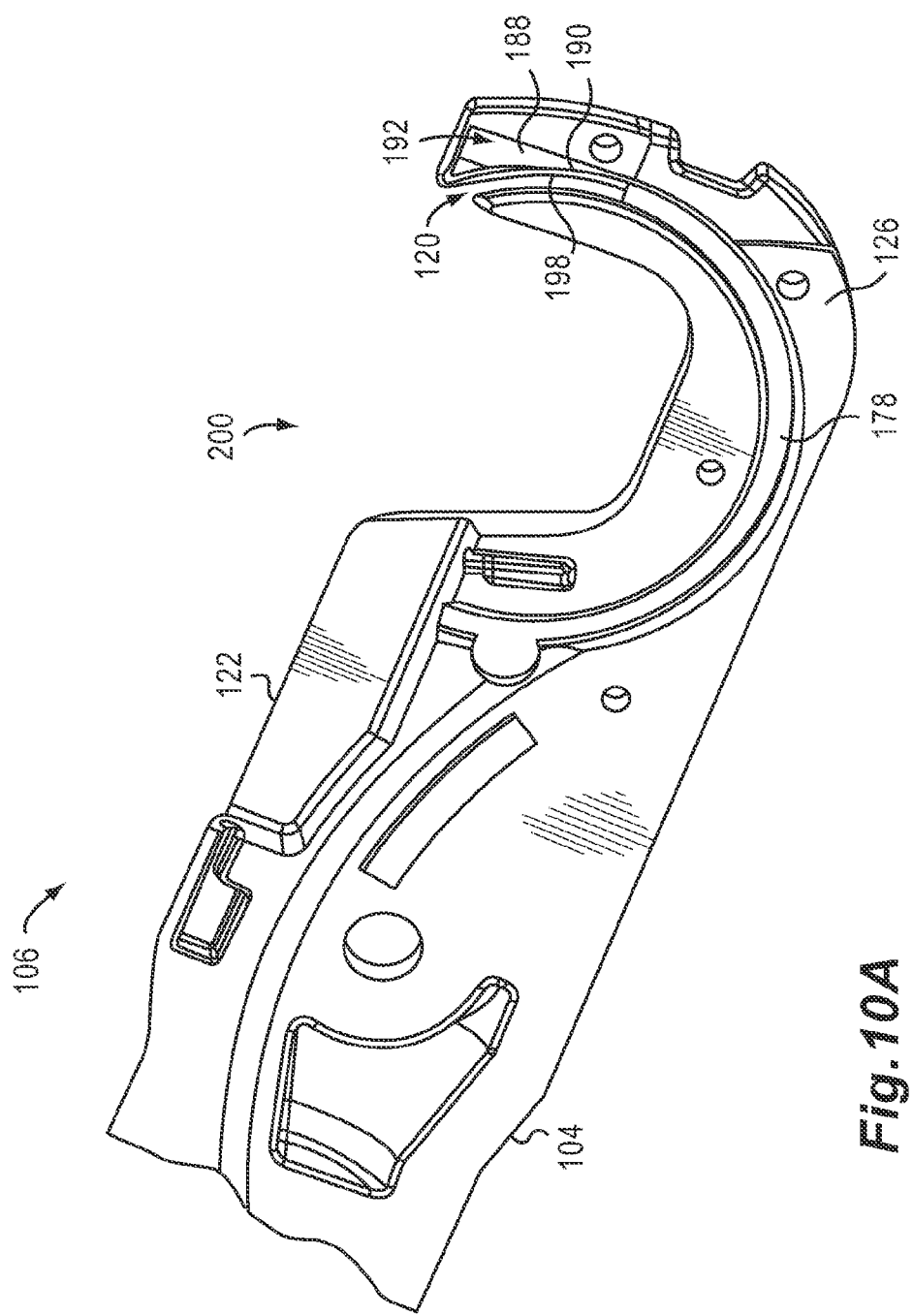
FIG. 10A is a partial schematic cross-sectional view of a distal portion of a suturing instrument in accordance with another embodiment of the invention.
Figure 10C:
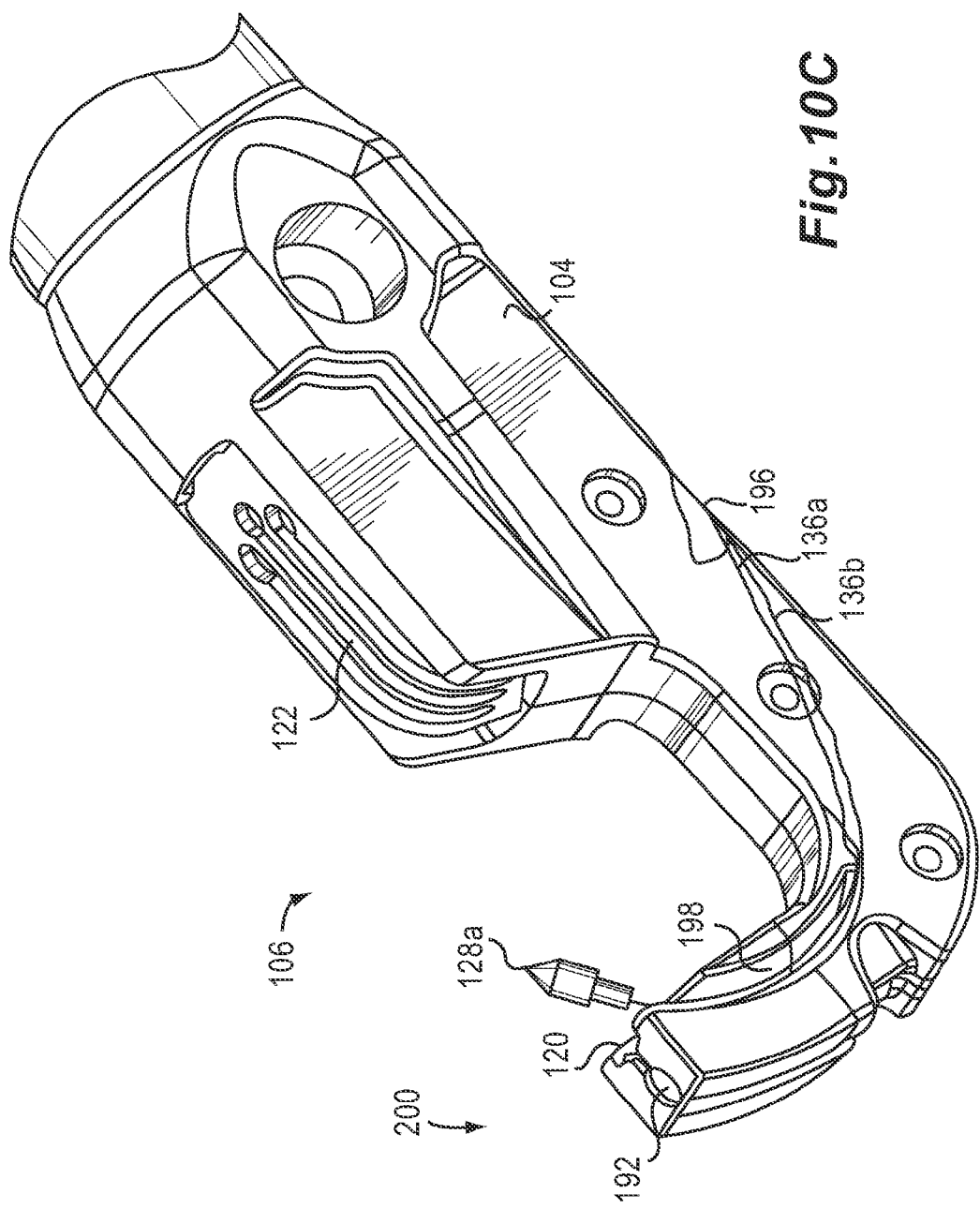

Referring to FIGS. 10A-10F, in an alternative embodiment, the distal portion 106 of the suturing instrument 100 includes a curved portion 200. The curved portion 200 defines a needle compartment 188, a needle output slot 190, a needle loading slot 192, a first suture slot 196 (FIG. 10B), and a second suture slot 198. In this embodiment, a needle 128*a* is inserted into the needle carrier 124 with a suture 136*a* extending through the needle carrier suture slot 148 (FIG. 7A), the first suture slot 196 and the second suture slot 198. An additional needle 128*b* is inserted into the needle compartment 188 through the needle loading slot 192 with a suture 136*b*-extending through the first suture slot 196 and the second suture slot 198 (FIG. 10B).

Figure 10D:
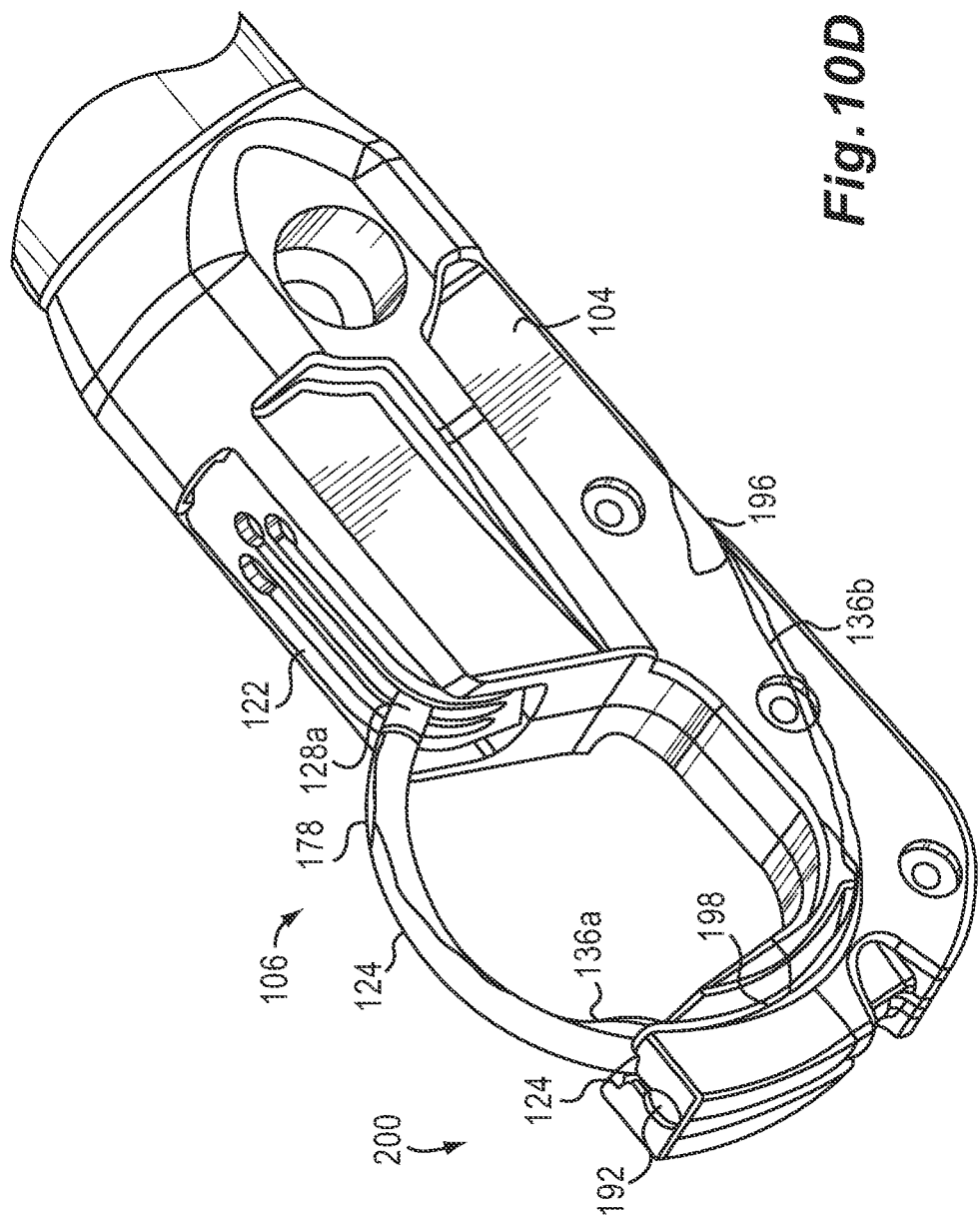
Figure 10E:
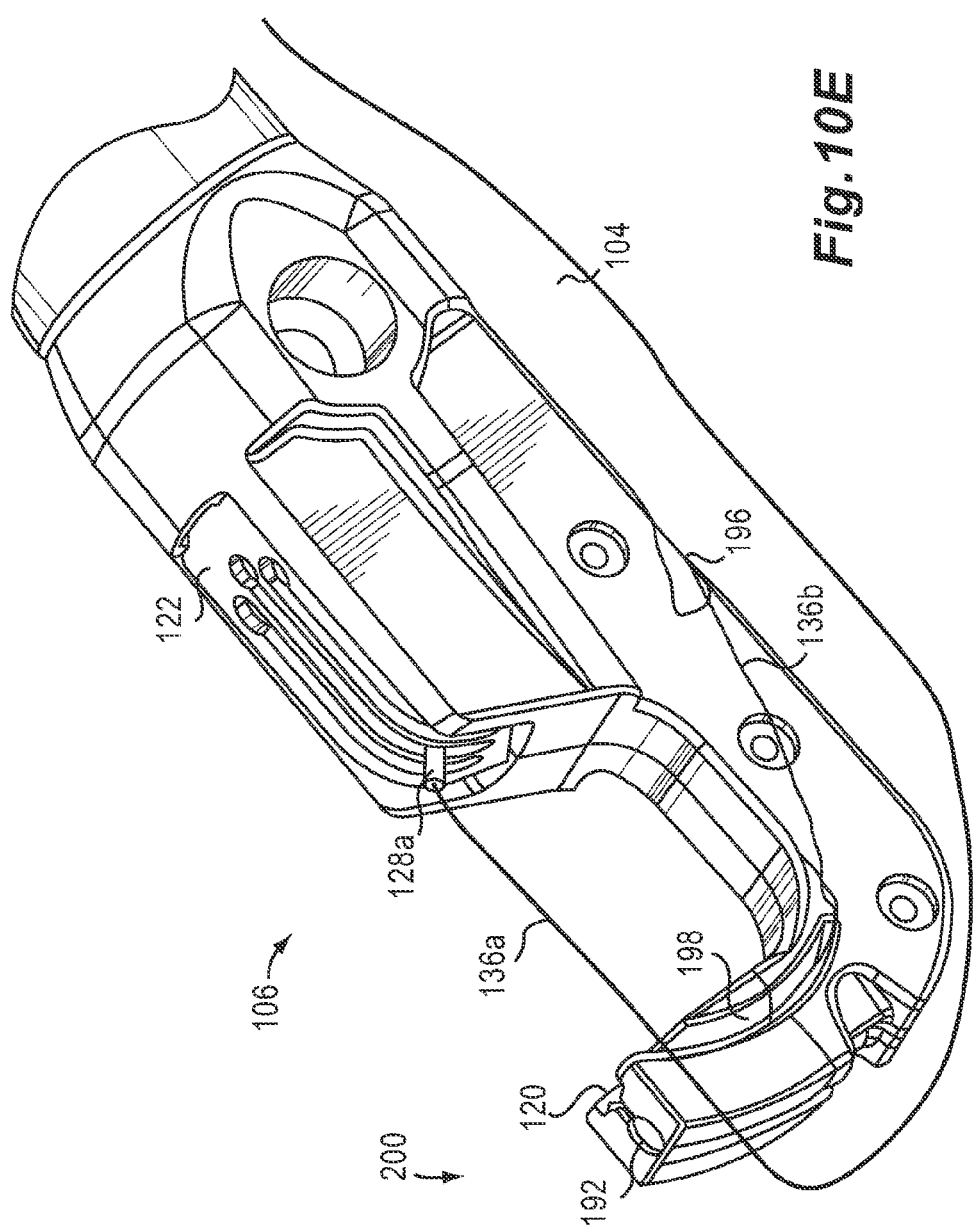

In operation, this alternative embodiment functions largely the same way as the embodiment previously described. The user advances the needle carrier 124 by pressing the button 117 (FIG. 1A) until the first needle 128*a* along with the first suture 136*a* is driven through the tissue and captured by the needle catch 122 (FIG. 10D). After the needle 128*a* and the suture 136*a* are captured in the needle catch 122, the needle carrier 124 is retracted so that the second needle 128*b* can be loaded into the needle carrier 124 (FIG. 10E). When the needle carrier 124 is fully retracted, the user pulls the second suture 136*b* causing the second needle 128*b* to slide into the needle carrier 124 from the needle compartment 188 through the needle loading slot 190. The user again advances the needle carrier 124 out of the needle exit port 120, through the tissue, and into the needle catch 122 (FIG. 10F). The user then retracts the needle carrier 124 leaving the needle 128*b* and coupled suture 136*b* captured by the needle catch 122. In other embodiments, more needles 128 and sutures 136 can be loaded into the needle compartment 188.

Figure 13:
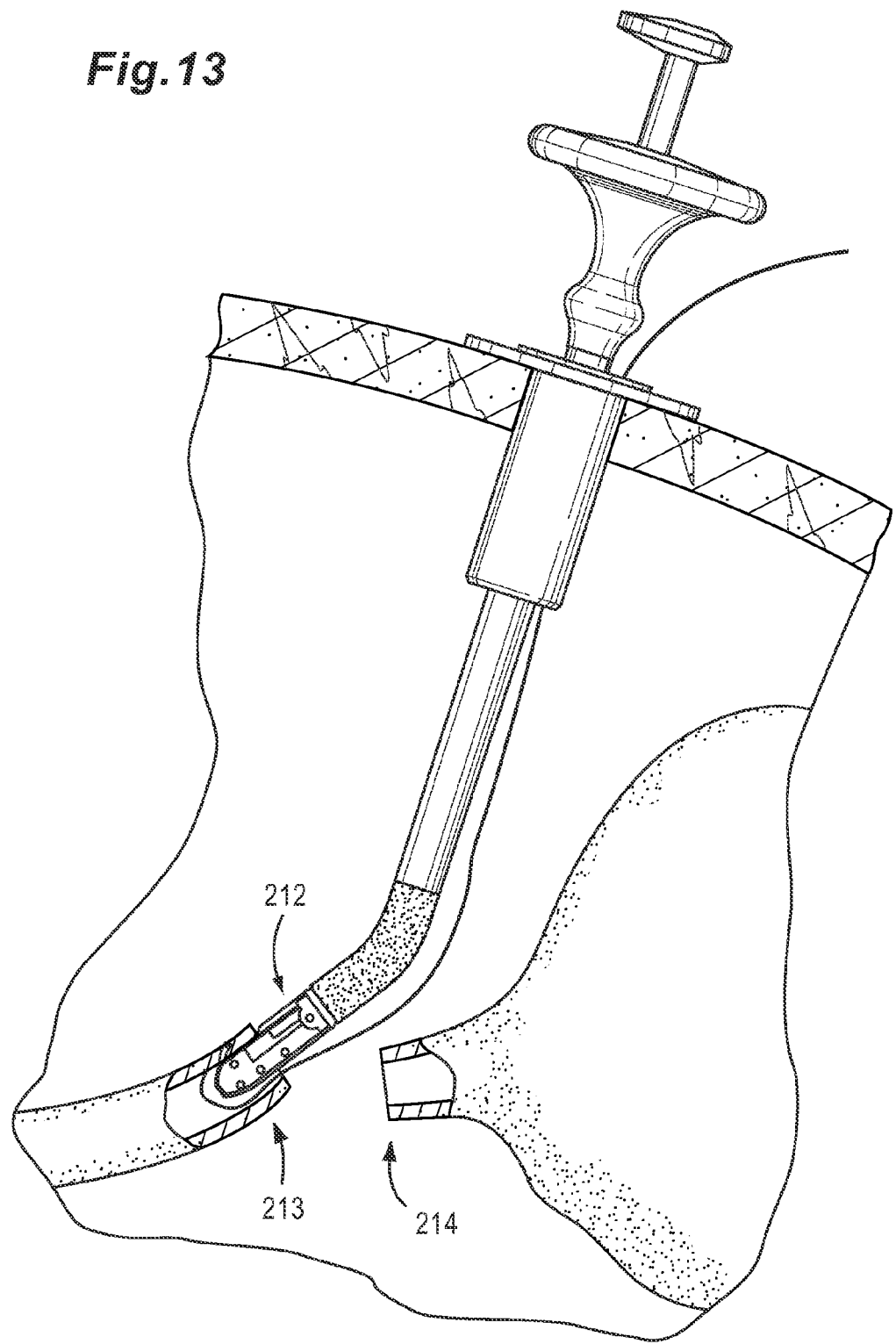
FIG. 13 is a side-view schematic illustration of the suturing instrument of FIG. 12 inserted into the abdominal cavity, with the suturing head inserted into the proximal end of a transected urethra. In this illustration, the upper portion of the body is located on the right.
Figure 14:
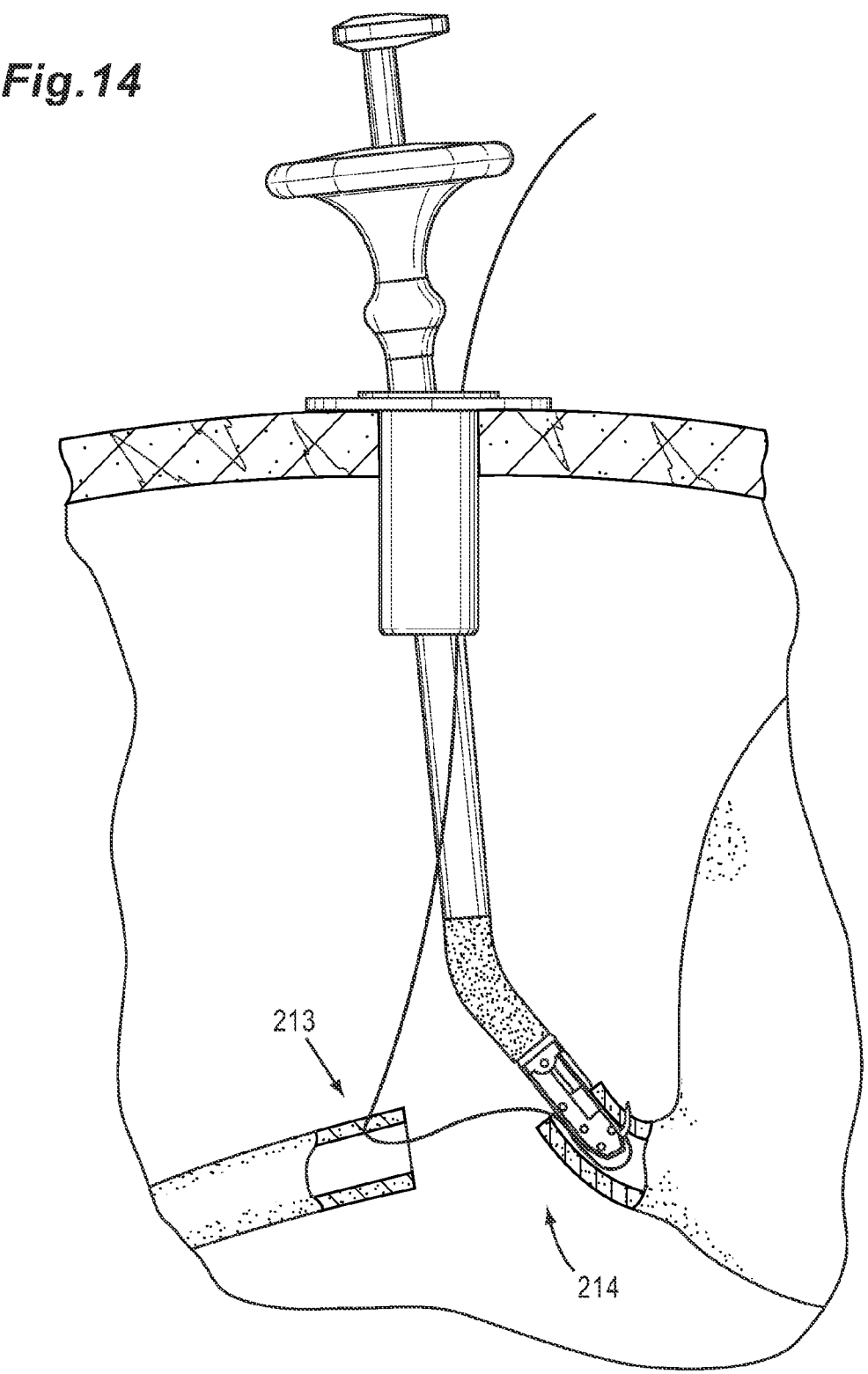
FIG. 14 is a side-view schematic illustration of the suturing instrument of FIG. 12 in the abdominal cavity oriented away from the transected urethra, with the suturing head inserted into the urethral orifice of the neck of the bladder.
Figure 15:
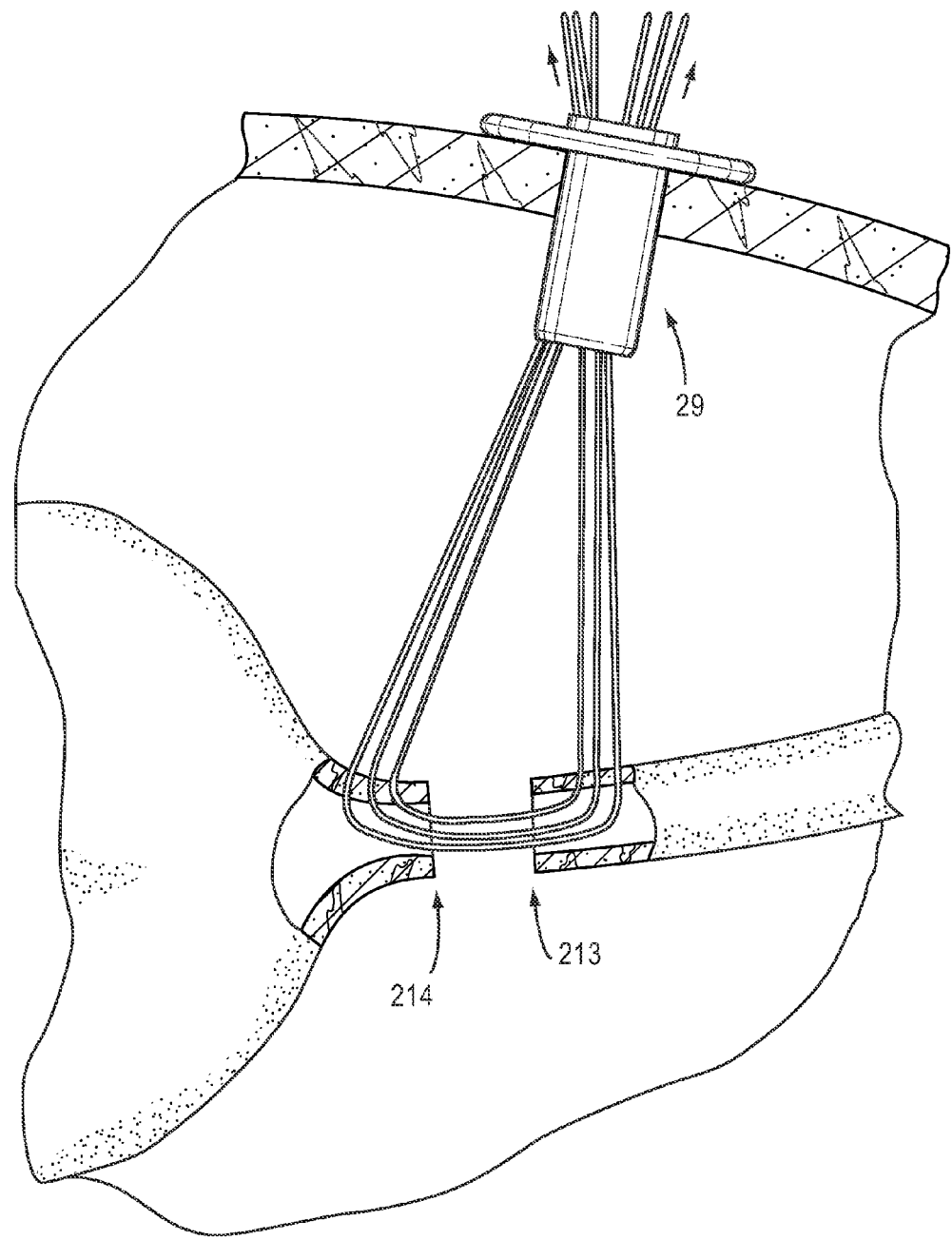
FIG. 15 is a schematic illustration of the suturing material having been threaded through the urethra and the neck of the bladder, with the suture ends brought out through the laparoscopic trocar cannula for subsequent tying and approximation of the urethra with the bladder. In this illustration, the upper portion of the body is located on the left.

FIGS. 12-15 schematically show an embodiment of the medical device 100 being used for laparoscopic radical prostatectomy, in which the transected urethra is anastomosed to the urethral orifice of the neck of the bladder. Because of the flexibility of the connector member 114, the surgeon can insert the suturing instrument 100 through the cannula of a trocar in the anterior abdominal wall. Once inside the abdominal cavity, the suturing head 107 bends at an angle relative to the elongate body member 104, either from externally applied force against the pelvic floor, or from the intrinsic properties of the connector member 114 (comprising, for example, either a pre-formed bent spring or polymeric material). As shown in FIG. 12, the suturing head 107 can then be inserted into the lumen of the transected urethra 213. Rotating the button 117 of the needle deployment mechanism causes the inner tube within the elongated body 104 to rotate about the long axis "X" of the elongate body member 104. This rotational movement is transmitted within the connector 114 through a ratchet assembly 210 in the suturing head 107 and rotates the suturing head 107 about its own axis "Y". The surgeon then actuates the needle deployment mechanism 110 by pushing on the button 117, deploying a suture in an inside-out fashion through the wall of the urethra, as shown in FIG. 13. In an embodiment, the outside surface of the suturing head 107 can be formed with a ridge 212 on at least one side that will stop the insertion of the suturing head 107 into the urethral lumen 213 at a pre-defined depth, allowing the instrument to reliably take an optimally sized 'bite' of tissue with the suturing needle. As shown in FIG. 14, after placement of a suture through the urethra, the suturing instrument 100 is turned in a proximal direction and inserted into the urethral orifice of the neck of the bladder 214. A second suture can then be placed, again in an inside-out fashion. In an embodiment, a single line of suture material is equipped with a needle on each end (double-armed suture), so that a single suture thread can be deployed between the distal urethra and the proximal bladder neck—one end first through the urethra, and the other end next through the urethral orifice of the bladder neck. As shown in FIG. 15, once the suture is placed through the urethra 213 and the bladder neck 214, the suturing instrument can then be withdrawn through the laparoscopic cannula 29, pulling the ends of the deployed suture material out of the abdominal cavity. At that point, each needle 128 (as shown in FIG. 8A) can then be detached from the suture material 136, and a knot can be tied between the two ends of each suture 136. The surgeon can then use a knot pusher to slide the knot down into the surgical field, and approximate the urethra 213 to the bladder neck 214 by applying tension on the knotted thread.

Certain embodiments according to the invention have been disclosed. These embodiments are illustrative of, and not limiting on, the invention. Other embodiments, as well as various modifications and combinations of the disclosed embodiments, are possible and are within the scope of this disclosure.

What is claimed is:

1. A suturing instrument comprising:
 an elongate body member including a handle at a proximal portion and engaged to a suturing head at a distal portion by a connector member, the suturing head including a needle carrier and a needle catch, the suturing head defining a channel and a needle exit port, the needle carrier disposed within the channel, the needle carrier including a lumen for holding a needle with a tissue-penetrating tip, the needle catch for receiving and retaining the needle, the suturing head being rotatable about or relative to a longitudinal axis of the elongate body member, biased in a linear orientation relative to the longitudinal axis of the elongate body member, and adjustable to a plurality of non-linear orientations relative to the longitudinal axis of the elongate body member by application of an external force against the suturing head, the suturing head returning to the linear orientation in the absence of the external force; and an actuator manipulatable by a user of the suturing instrument to move the needle carrier in the channel and out of the needle exit port until the needle enters the needle catch where the needle is retained.

2. The suturing instrument of claim 1, wherein the connector member comprises a spring.

3. The suturing instrument of claim 1, wherein the connector member comprises a plurality of springs.

4. The suturing instrument of claim 1, wherein the connector member comprises a polymer.

5. The suturing instrument of claim 1, wherein the connector member comprises a flexible plastic.

6. The suturing instrument of claim 4, wherein the polymer comprises a flexible polymer.

7. The suturing instrument of claim 1, wherein the connector member is a flexible connector member.

* * * * *